US006534036B1

United States Patent
(12) Collinge et al.

(10) Patent No.: US 6,534,036 B1
(45) Date of Patent: Mar. 18, 2003

(54) BIOLOGICAL MATERIALS AND METHODS USEFUL IN THE DIAGNOSIS AND TREATMENT OF DISEASES

(75) Inventors: John Collinge, London (GB); Anthony R. Clarke, London (GB); Graham S. Jackson, London (GB)

(73) Assignee: D. Gen Limited, London (GB)

( * ) Notice: Subject to any disclaimer, the term of this patent is extended or adjusted under 35 U.S.C. 154(b) by 0 days.

(21) Appl. No.: 09/431,887

(22) Filed: Nov. 2, 1999

(30) Foreign Application Priority Data

Nov. 4, 1998 (GB) .............................................. 9824091
Mar. 18, 1999 (GB) .............................................. 9906217

(51) Int. Cl.[7] ........................ A61K 49/00; A61K 39/00; A61K 45/00; C12N 5/00

(52) U.S. Cl. ...................... 424/9.1; 424/9.2; 424/184.1; 424/185.1; 424/278.1; 435/325; 530/300; 530/350

(58) Field of Search ....................... 424/9.1, 9.2, 184.1, 424/185.1, 278.1; 435/325; 530/300, 350

(56) References Cited

U.S. PATENT DOCUMENTS 5,846,533 A 12/1998 Prusiner et al.

FOREIGN PATENT DOCUMENTS

| | | | |
|---|---|---|---|
| EP | 302 473 A2 | 8/1989 | A61K/39/395 |
| EP | 0 861 900 | 2/1997 | |
| EP | 815 872 A2 | 7/1998 | A61K/47/48 |
| WO | WO 88/07378 | 10/1988 | A61K/39/395 |
| WO | WO 91/11201 | 8/1991 | A61K/47/48 |
| WO | WO 93/23432 | 11/1993 | C07K/13/00 |
| WO | WO96/39834 | 12/1996 | A01N/43/40 |
| WO | WO 98/16834 | 4/1998 | G01N/33/68 |
| WO | WO 98/20022 | 5/1998 | C07K/1/00 |
| WO | WO 98/37210 | 8/1998 | C12N/15/70 |
| WO | WO 98/37411 | 8/1998 | |
| WO | WO 98/55132 | 12/1998 | A61K/38/00 |

OTHER PUBLICATIONS

Jack Nguyen, Michael A. Baldwin, Fred E. Cohen and Stanley B. Prusiner, "PRION Protein Induce α–Helix to β–Sheet Conformational Transitions", Biochemistry 1995, 34, pp. 4186–4192.
Current Opinion in Structural Biology, 1997, 7:53–59, PM Harrison et al., "The Prion Folding Problem".
Scott et al., "Identification of a Prion Protein Epitope Modulating Transmission of Bovine Spongiform Encephalopathy Prions to Transgenic Mice", Proc. Nat'l. Acad. Sci. USA, vol. 94, pp. 14279–14284, Dec. 1997.
Hosszu et al., "Structural Mobility of the Human Prion Protein Probed by Backbone Hydrogen Exchange", Nature Structural Biology, vol. 6, No. 8, pp. 740–743, Aug. 1999.

Ingrid Mehihorn, Darlene Groth, Johanne Stockel, Barbara Moffat, et al., "High–Level Expression and Characterization of a Purified 142–Residue Polypeptide of the Prion Protein", *Biochemistry* 1996, 35, 5528–5537.

C. Korth, B. Stierl, P. Streit, M. Moser, et al., "Prion (PrP)–Specific Epitope Defined by a Monoclonal Antibody", *Letters to Nature*, XP–002092791, 74–77.

Hong Zhang, Johannes Stocket, Ingrid Mehihorn, Darlene Groth, et al., "Physical Studies of Conformational Plasticity in a Recombinant Prion Protein", *Biochemistry* 1997, 36, 3543–3553.

Wieslaw Swietnicki, Robert Petersen, et al., *pH–Dependent Stability and Conformation of the Recombinant Human Prion Protein* PrP(90–231), *Communication, The Journal of Biological Chemistry* XP2137000, vol. 272, No. 44, Oct. 31, 1997, pp. 27517–27520.

Simone Hornemann and Rudi Glockshuber, "A Scrapie–Like Unfolding Intermediate of the Prion Protein Domain PfP(121–231) Induced by Acidic pH", *Biochemistry Proc. Natl. Acad. Sci. USA*, vol. 95, pp. 6010–6014, May 1998.

J. Safar, "The Folding Intermediate Concept of Prion Protein Formation and Conformational Links to Infectivity", *Laboratory of Central Nervous Sysem Studies, National Institutes of Health*, XP–000887028, May 16, 2000, pp. 69–76.

Jack Nguyen, Michael A. Baldwin, Fred E. Cohen and Stanley B. Prusiner, "Prion Protein Peptides Induce α–Helix to β–Sheet Conformational Transitions", *Biochemistry* 1995, 34, 4186–4192.

Luca De Gioia, Carlo Selvaggini, Elene Ghibaudi, et al., "Conformational Polymorphism of the Amyloidogenic and Neurotoxic Peptide Homologous to Residues 106–126 of the Prion Protein", *Journal of Biological Chemistry*, vol. 269, No. 11, Mar. 18, 1994, pp. 7859–7862.

Michael A. Baldwin, Fred E. Cohen and Stanley B. Prusiner, "Prion Protein Isoforms, a Convergence of Biological and Structural Investigations", *Minireview, The Journal of Biological Chemistry* XP–002074799, vol. 270, No. 33, Aug. 18, 1995, pp. 19197–19200.

Tamaki Muramoto, Michael Scott, and Fred E. Cohen and Stanley B. Prusiner, "Recombinant Scrapie–Like Prion Protein of 106 Amino Acids is Soluble", *Neurobiology, Proc. Natl. Acad. Sci. USA*, vol. 93, pp. 15457–15462, Dec. 1996.

(List continued on next page.)

*Primary Examiner*—Rodney P Swartz
(74) *Attorney, Agent, or Firm*—C. G. Mersereau; Nikolai & Mersereau, P.A.

(57) ABSTRACT

The present invention relates to a method of making a β-form of a prion protein which preferably has more β-sheet than α-helix structure and is soluble in the absence of a denaturant and/or is non-aggregated and exhibits partial resistance to digestion with proteinase K. The invention also relates to use of the β-form in medicine, especially for raising antibodies useful in the treatment and/or diagnosis of prion diseases. The invention also relates to methods of screening for compounds which are capable of inhibiting and/or reversing the conversion of the native α-form of a prion protein to a β-form, and to uses of identified compounds in medicine.

5 Claims, 10 Drawing Sheets

OTHER PUBLICATIONS

Figure 1A:
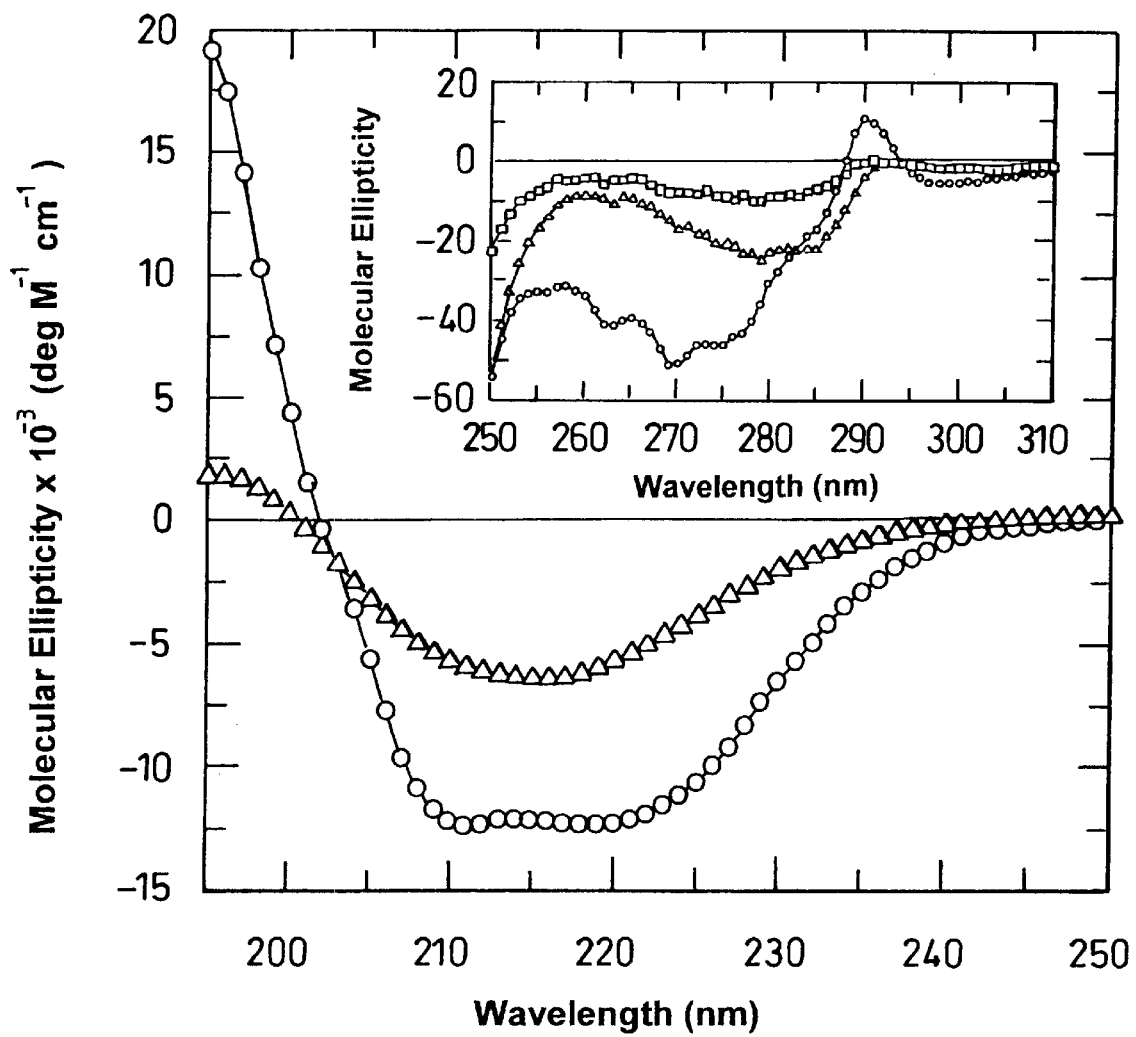

Jiri Safar, Peter P. Roller, D. Carleton Gajdusek and Clarence J. Gibbs, Jr., "Scrapie Amyloid (Prion) Protein has the Conformational Characteristics Aggregated Molten Globule Folding Intermediate", *Laboratory of Central Nervous System Studies, National Institutes of Health, Biochemistry* 1994, 33, 8375–8383, XP–000909430, 1994 American Chemical Society.

G.S. Jackson, L.L.P. Hosszu, A. Power, A.F. Hill, et al., "Reversible Conversion of Monomeric Human Prion Protein Between Native and Fibrilogenic Conformations", *Science*, XP–000887243, vol. 283, pp. 1935–1937, Mar. 19, 1999.

Jonathan DF Wadsworth, Graham S. Jackson, Andrew F. Hill and John Colligne, "Molecular Biology of Prion Propagation", *Current Opinion in Genetics & Development*, 1989, 9:338–345.

Alexandrescu, A.T., Evans, P.A., Pitkeathly, M., Baum, J. & Dobson, C.M. (1993) *Biochemistry* 32:1707–1718.

Bagshawe (1987) *Brit. J. Cancer* 56:531–532.

Bagshawe et al. (1988) *Brit. J. Cancer* 58:700–703.

Büeler (1992) *Nature* 356:577–582.

Bridgewater et al. (1995) *Eur. J. Cancer* 31A:2362–2370.

Chen Y.H., Yang J.T. & Martinex H.M. (1972) *Biochemistry* 11:4120–4131.

Chyan C.L., Wornald C., Dobson C.M., Evans, P.A. & Baum J. (1993) *Biochemistry*, 32:5681–5691.

Clarke A.R. & Waltho J.P. (1997) *Curr. Opin. Biotechnol.* 8:400–410.

Colligne J. (1997) *Hum. Mol. Genetics* 6:1699–1705.

Colligne J., Palmer M.S. & Dryden A.J. (1991) *Lancet* 337:1441–1442.

Colligne et al. (1995) *Lancet* 346:569–570.

Colligne et al. (1996) *Nature* 383:685–690.

Devereux et al. (1984) *Nucl. Acids Res.* 12:387–395.

Eliezer D., Yao J., Dyson H. J. & Wright P.E. (1998) *Nat. Struct. Biol.* 5:148–155.

Ezzeddine et al. (1991) *New Biol.* 3:608–614.

Fink (1998) *Folding and Design* 3:R9–23.

Fink (1997) *Folding and Design* 3:19–25.

Fischer (1996) *EMBO J.* 15:1255–1264.

Hawke et al. (1992) *J. Immunol. Methods* 155:41–48.

Hnatowich et al. (1988) *J. Nucl. Med.* 29:1428–1434.

Hornemann S. & Glockshuber R. (1996) *J. Mol. Bilol.* 261:614–619.

Hornemann S. & Glockshuber R. (1998) *Proc. Natl. Acad. Sci. USA* 95:6010–6014.

Jackson et al (1999) *Science* 283:1935–7.

James T.L., Liu H., Ulyanov H.B. et al. (1997) *Proc. Natl. Acad. Sci. USA* 94:10086–10091.

Korth et al. (1997) *Nature* 390:74–77.

Leo et al. (1987) *Proc. Natl. Acad. Sci. USA* 84:1374–78.

Mehhorn et al. (1996) *Biochem* 35:5528–37.

Moolten (1986) *Cancer Res.* 46:5276–5281.

Neuberger et al. (1984) *Nature* 312:604–609.

Paganelli et al. (1990) *Int. J. Cancer* 45:1184–1189.

Pan K.M., Baldwin M.A., Nguyen J., et al. (1993) *Proc. Natl. Acad. Sci. USA*, 90:10962–10966.

Prusiner S.B. (1991) *Science*, 252:1515–1522.

Ptitsyn O.B. (1994) *Protein Eng.* 7:593–596.

Ptitsyn O.B. (1995) *Adv. Protein Chem.* 47:83–229.

Ptitsyn O.B. (1995) *Curr. Opin. Struct. Biol.* 5:74–78.

Ptitsyn O.B. [news] (1996) *Nat. Struct. Biol.* 3:488–490.

Ptitsyn O.B. et al. (1995) *Philo. Trans. R. Soc. Land. B. Biol Sci*; 348:35–41.

Riek R., Hornemann S., Wider G., Billeter M., Glockshuber R. & Wuthrich K. (1996) *Nature* 382:180–182.

Safar et al. (1993) *J. Biol. Chem* 268:20276–20284.

Senter (1988) *Proc. Nat. Acad. Sci. USA* 85:4842–4846.

Shyng et al. (1993) *J. Biol. Chem.* 268:15922–8.

Swietnicki et al. (1997) *J. Biol. Chem.* 272(44):27517–27520.

Swietnicki et al. (2000) *J. Biol. Chem.* 39:424–431.

Zahn R., Von Schroetter C. & Wüthrich K. (1997) *FEBS Lett.* 417:400–404.

Zhan et al. (1994) *Biochem.* 33:11254–63.

Zhang et al. (1997) *Biochem.* 36(12):3543–3553.

PK µg/ml

α - PrP

Soluble
β - PrP

Aggregated
β - PrP

| | | | | |
|---|---|---|---|---|
| Human | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Chimpanzee | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Orangutan | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Gorilla | : | ------MANLGCWMLVLFVATWSNLGLCKK-RPKPGG-WNTGGS-RYPGQ-GSPGGNRYPPQG------GGGWGQPHGGG---WGQPHGGGWGQPHGGGW | : | 87 |
| Monkey(Gr) | : | ------MANLGCWMLVLFLFVATWSDLGLCKK-RPKPGG-WNTGGS-RYPGQ-GSPGGNRYPPQG------GGGWGQPHGGG---WGQPHGGGWGQPHGGGW | : | 87 |
| Monkey(S) | : | ------MANLGCWMLVVFVATWSDLGLCKK-RPKPGG-WNTGGS-RYPGQ-GSPGGNRYPPQG---------GGG---WGQPHGGGWGQPHGGGW | : | 79 |
| Rhesus | : | ------MANLGCWMLVLFVATWSDLGLCKK-RPKPGG-WNTGGS-RYPGQ-GSPGGNRYPPQG--GGWGQPHGGGWGQPHGGG---WGQPHGGGWGQPHGGGW | : | 94 |
| Gibbon | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Macaque(S) | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Macaque(C) | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Macaque(J) | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Macaque(P) | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Marmoset | : | ------MANLGCWMLFLFVATWSDLGLCKK-RPKPGG-WNTGGS-RYPGQ-GSPGGNRYPPQG------GGGWGQPHGGG---WGQPHGGGWGQPHGGGW | : | 87 |
| Hamadryas | : | ------MANLGCWMLVLFVATWSDLGLCKK-RPKPGG-WNTGGS-RYPGQ-GSPGGNRYPPQ-------GGGWGQPHGGG---WGQPHGGGWGQPHGGGW | : | 86 |
| Cercopithe | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Guereza | : | ------MANLGCWMLVVFVATWSDLGLCKK-RPKPGG-WNTGGS-RYPGQ-GSPGNLYPPQ----------GGG---WGQPHGGGWGQPHGGGW | : | 79 |
| Capuchin | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Francoisi | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGH | : | 86 |
| Siamang | : | ------MANLGCWMLVLFVATWSDLGLCKK-RPKPGG-WNTGGS-RYPGQ-GSPGGNRYPPQG------GGGWGQPHGGG---WGQPHGGGWGQPHGGGW | : | 87 |
| Mouse(RML) | : | ------MANLGYWLLALFVTMWTDVGLCKK-RPKPGG-WNTGGS-RYPGQ-GSPGGNRYPPQ-------GGTWGQPHGGG---WGQPHGGSWGQPHGGGW | : | 87 |
| Mouse(Sh) | : | ------MANLGYWLLALFVTMWTDVGLCKK-RPKPGG-WNTGGS-RYPGQ-GSPGGNRYPPQ-------GGTWGQPHGGG---WGQPHGGSWGQPHGGSW | : | 86 |
| Mouse(Lg) | : | ------MANLGYWLLALFVTMWTDVGLCKK-RPKPGG-WNTGGS-RYPGQ-GSPGGNRYPPQ-------GGTWGQPHGGG---WGQPHGGSWGQPHGGSW | : | 86 |
| Hamster(C) | : | ------MANLSYWLLALFVATWTDVGLCKK-RPKPGG-WNTGGS-RYPGQ-GSPGGNRYPPQ-------GGTWGQPHGGG---WGQPHGGGWGQPHGGSW | : | 86 |
| Cow | : | -----MVKSHIGSWILVLFVAMWSDVGLCKK-RPKPGGWNTGGS-RYPGQ-GSPGGNRYPPQGGGGWGQPHGGGWGQPHGGGW---WGQPHGGGWGQPHGGGW | : | 96 |
| Sheep | : | -----MVKSHIGSWILVLFVAMWSDVGLCKK-RPKPGGWNTGGS-RYPGQ-GSPGGNRYPPQG------GGGWGQPHGGG---WGQPHGGGWGQPHGGGW | : | 87 |
| Antelope | : | ----MVKSHIGSWILVLFVAMWSDVALCKK-RPKPGGGWNTGGS-RYPGQ-GSPGGNRYPPQG------GGGWGQPHGGG---WGQPHGGGWGQPHGGGW | : | 84 |
| Kudu | : | ----MVKSHIGSWILVLFVAMWSDVGLCKK-RPKPGGGWNTGGS-RYPGQ-GSPGGNRYPSQGGGGGWGQPHGGGWGQPHGGGW---WGQPHGGGWGQPHGGGW | : | 96 |
| Goat | : | ----MVKSHIGSWILVLFVAMWSDVGLCKK-RPKPGGGWNTGGS-RYPGQ-GSPGGNRYPPQG------GGGWGQPHGGG---WGQPHGGGWGQPHGGGW | : | 88 |
| Pig | : | ----MVKSHIGGWILVLFVAAWSDIGLCKK-RPKPGGGWNTGGS-RYPGQ-GSPGGNRYPPQG------GGGWGQPHGGG---WGQPHGGGWGQPHGGGW | : | 88 |
| Polecat | : | ----MVKSHIGGWILVLFVATWSDIGFCKK-RPKPGGGWNTGGGS-RYPGQ-GSPGGNRYPPQG-----GGGWGQPHGGG---WGQPHGGGWGQPHGGGW | : | 88 |
| Dog | : | ----MVKSHIGGWIL-LFVATWSDVGLCKK-RPKPGGGWNTGGGS-RYPGQ-GSPGGNRYPPQG-----GGGWGQPHGGG---WGQPHGGGWGQPHGGGW | : | 87 |
| Rabbit | : | ----MAHLGYWMLLLFVAMWSDLGLGLCKKIPKPGGGWNSGGSNRYPGQPGSPGGNRYPGWGHPQGG--GGGWGQPHGGG---WGQPHGGGWGQPHGGGW | : | 96 |
| Marsupial | : | ------MGKIQLGYWILVLFTPCCLLALLAACTDVALSKKGKGKPSGGGWGAGSHRQPSYPRQPG----YPHNPGYPHNPGYPHNPGYPHNPGYPNPGYPHNPGY | : | 92 |
| Chicken | : | MPAAMARLLTTCCLLALLAACTDVALSKKGKGKPSGGGWGAGSHRQPSYPRQPG---YPHNPGYPHNPGYPHNPGYPHNPGYPNPGYPHNPGY | : | 98 |

*Fig. 6*

```
Human       : GQPH-GGGWGQGGGTHSQWNKPSK-PKTNMKHMAGAAAAGAVVGGLGGYMLGSAMSRPIIHFGSDYEDRYYRENMHRYPNQVYYRPMDEYSNQNNFVHDCV    186
Chimpanzee  : GQPH-GGGWGQGGGTHSQWNKPSK-PKTNMKHMAGAAAAGAVVGGLGGYMLGSAMSRPIIHFGSDYEDRYYRENMHRYPNQVYYRPMDQYSSQNNFVHDCV    186
Orangutan   : GQPH-GGGWGQGGGTHSQWNKPSK-PKTNMKHMAGAAAAGAVVGGLGGYMLGSAMSRPIIHFGSDYEDRYYRENMHRYPNQVYYRPVDQYSNQNNFVHDCV    186
Gorilla     : GQPH-GGGWGQGGGTHSQWNKPSK-PKTNMKHMAGAAAAGAVVGGLGGYMLGSAMSRPIIHFGNDYEDRYYRENMHRYPNQVYYRPVDQYSNQNNFVHDCV    186
Monkey(Gr)  : GQPH-GGGWGQGGGTHNQWNKPSK-PKTNMKHMAGAAAAGAVVGGLGGYMLGSAMSRPLIHFGSDYEDRYYRENMRYPNQVYYRPMDQYSNQNNFVHDCV     178
Monkey(S)   : GQPH-GGGWGQGGGTHNQWNKPSK-PKTNMKHMAGAAAAGAVVGGLGGYMLGSAMSRPLIHFGSDYEDRYYRENMRYPNQVYYRPVDQYSNQNNFVHDCV     193
Rhesus      : GQPH-GGGWGQGGGTHNQWHKPSK-PKTSMKHMAGAAAAGAVVGGLGGYMLGSAMSRPLIHFGNDYEDRYYRENMRYPSQVYYRPVDQYSNQNNFVHDCV     186
Gibbon      : GQPH-GGGWGQGGGTHNQWHKPSK-PKTSMKHMAGAAAAGAVVGGLGGYMLGSAMSRPLIHFGNDYEDRYYRENMRYPNQVYYRPVDQYSNQNNFVHDCV     186
Macaque(S)  : GQPH-GGGWGQGGGTHNQWHKPSK-PKTSMKHMAGAAAAGAVVGGLGGYMLGSAMSRPIIHFGSDYEDRYYRENMRYPNQVYYRPMDQYSSQNNFVHDCV     186
Macaque(C)  : GQPH-GGGWGQGGGTHNQWHKPSK-PKTSMKHMAGAAAAGAVVGGLGGYMLGSAMSRPLIHFGNDYEDRYYRENMRYPNQVYYRPVDQYSNQNNFVHDCV     186
Macaque(J)  : GQPH-GGGWGQGGGTHNQWHKPSK-PKTSMKHMAGAAAAGAVVGGLGGYMLGSAMSRPLIHFGNDYEDRYYRENMRYPNQVYYRPVDQYSNQNNFVHDCV     186
Macaque(P)  : GQPH-GGGWGQGGGTHNQWHKPSK-PKTSMKHMAGAAAAGAVVGGLGGYMLGSAMSRPLIHFGN?YEDRYYRENMRYPNQVYYRPVDQYSNQNNFVHDCV     186
Marmoset    : GQPH-GGGWGQGGGTHSQWNKPSK-PKTNMKHVAGAAAAGAVVGGLGGYMLGSAMSRPLIHFGNLYEDRYYRENMRYPNQVYYRPVDQYNNQNNFVHDCV     186
Hamadryas   : GQPH-GGGWGQGGGTHNQWHKPSK-PKTSMKHMAGAAAAGAVVGGLGGYMLGSAMSRPLIHFGNDYEDRYYRENMRYPNQVYYRPVDQYSNQNNFVHDCV     185
Cercopithe  : GQPH-GGGWGQGGGTHNQWHKPSK-PKTSMKHMAGAAAAGAVVGGLGGYMLGSAMSRPLIHFGNDYEDRYYRENMRYPNQVYYRPVDQYSNQNNFVHDCV     186
Guereza     : GQPH-GGGWGQGGGTHSQWNKPSK-PKTSMKHMAGAAAAGAVVGGLGGYMLGSAMSRPLIHFGNDYEDRYYRENMRYPNQVYYRPVDQYSNQNNFVHDCV     178
Capuchin    : GQPH-GGGWGQGGGTHNQWNKPSK-PKTSMKHVAGAAAAGAVVGGLGGYMLGSAMSRPLIHFGNDYEDRYYRENMRYPNQVYYRPVDQYSNQNNFVHDCV     186
Francoisi   : GQPH-GGGWGQGGGTHNQWNKPSK-PKTSMKHVAGAAAAGAVVGGLGGYMLGSAMSRPIIHFGSDYEDRYYRENMRYPNQVYYRPVDQYSNQNNFVHDCV     186
Siamang     : GQPH-GGGWGQGGGTHNQWNKPSK-PKTNLKHVAGAAAAGAVVGGLGGYMLGSAMSRPLIHFGNDYEDRYYRENMRYPNQVYYRPVDQYSNQNNFVHDCV     185
Mouse(RML)  : GQPH-GGGWGQGGGTHNQWNKPSK-PKTNLKHVAGAAAAGAVVGGLGGYMLGSAVSRPMIHFGNDYWEDRYYRENMRYRYPNQVYYRPMDQYSSQNNFVHDCV  186
Mouse(Sh)   : GQPH-GGGWGQGGGTHNQWNKPSK-PKTNFKHVAGAAAAGAVVGGLGGYMLGSAMSRPMIHFGNDWEDRYYRENMRYRYPNQVYYRPVDQYSNQNNFVHDCV   185
Mouse(Lg)   : GQPH-GGGWGQGGGTHNQWNKPSK-PKTNMKHVAGAAAAGAVVGGLGGYMLGSAMSRPMLHFGNDWEDRYYRENMRYPNQVYYRPVDQYNNQNNFVHDCV     185
Hamster(C)  : GQPHGGGWGGWGQ-GGTHGQWNKPSK-PKTNMKHVAGAAAAGAVVGGLGGYMLGSAMSRPLIHFGSDYEDRYYRENMRYPNQVYYRPVDQYSNQNNFVHDCV   186
Cow         : GQPHGGGWGGWGQ-GGSHSQWNHPSK-PKTNMKHVAGAAAAGAVVGGLGGYMLGSAMNRPLIHFGNDYEDRYYRENMRYPNQVYYRPVDQYSNQNNFVHDCV   186
Sheep       : GQPHGGGWGGWGQ-GGTHSQWNKPSK-PKTSNMKHVAGAAAAGAVVGGLGGYMLGSAMSRPLIHFGSDYEDRYYRENMRYRYPNQVYYRPVDQYSNQNNTFVHDCV  195
Antelope    : GQPHGGGWGGWGQ-GGTHGQWNHPSK-PKTSMKHVAGAAAAGAVVGGLGGYMLGSAMSRPLIHFGSDYEDRYYRENMRYPNQVYYRPVDQYNNQNTFVHDCV   183
Kudu        : GQPHGGGWGGWGQ-GGTHGQWNHPSK-PKTSMKHVAGAAAAGAVVGGLGGYMLGSAMSRPLIHFGSDYEDRYYRENMRYPNQVYYRPVDQYSNQNNFVHDCV   187
Goat        : GQPHGGGWGGWGQ-GGSHSQWNKPSK-PKTNMKHVAGAAAAGAVVGGLGGYMLGSAMSRPLIHFGSDYEDRYYRENMRYPNQVYYRPVDQYSNQNSFVHDCV   195
Pig         : GQPHGGGWGGGSHGQWNKPSK-PKTNMKHVAGAAAAAGAVVGGLGGYMLGSAMSRPLIHFGSDYEDRYYRENMRYPNQVYYRPVDQYSNQNSFVHDCV       187
Polecat     : GQPHGGGWGGQGGSHGQWGKPCPK-PKTNMKHVAGAAAAAGAVVGGLGGYMLGSAMSRPLIHFGNDYEDRYYRENMRYPNQVYYRPVDQYSNQNNLVHDCV    188
Dog         : GQPHGGGWGGQGGSHSQWGKPNK-PKTNMKHVAGAAAAGAVVGGLGGYMLGSAMSRPVIHFGNEYEDRYYRENMRYPEQVYYRPVDQYSNQNNLVHDCV      188
Rabbit      : GQPHGGGWGQ-GGTHNQWGKPSK-PKTSMKHVAGAAAAGAVVGGLGGYMLGSAMSRPLIHFGNEYEDRYYRENQYRYPNQVMYRPIDQYSSQNNFVHDCV     187
Marsupial   : GQPHGGSNWGQGG--YNKW-KPDK-PKTNLKHVAGAAAAGAVVGGLGGYAMGRVMSGMNYHFDSPDEXRWWSENSARYPNRVYYRDYSSPVPQDVFVADCV   185
Chicken     : PGWGQYNPSSGGSYHNQ--KPWKPPKTNFKHVAGAAAAGAVVGGLGGYAMGRVMSGMNYHFDSPDEXRWWSENSARYPNRVYYRDYSSPVPQDVFVADCF  197
```

*Fig. 6* (continued)

```
Human        : NITIKQHTV-TTTTKGENFTETDVKMMERVVEQMCITQYERES--QAYY--QRGSSMVLFSSPPVILL--ISFLIFLIVG---   260
Chimpanzee   : NITIKQHTV-TTTTKGENFTETDVKMMERVVEQMCITQYERES--QAYY--QRGSSMVLFSSPPVILL--ISFLIFLIVG*--   260
Orangutan    : NITIKQHTV-TTTTKGENFTETDVKMMERVVEQMCITQYERES--QAYY--QRGSSMVLFSSPPVILL--ISFLIFLIVG*--   260
Gorilla      : NITIKQHTV-TTTTKGENFTETDVKMMERVVEQMCITQYERES--QAYY--QRGSSMVLFSSPPVILL--ISFLIFLIVG*--   260
Monkey(Gr)   : NITIKQHTV-TTTTKGENFTETDVKMMERVVEQMCITQYEKES--QAYY--QRGSSMVLFSSPPVILL--ISFLIFLIVG*--   252
Monkey(S)    : NVTIKQHTV-TTTTKGENFTETDVKMMERVVEQMCITQYEKES--QAYY--QRGSSMVLFSSPPVILL--ISFLIFLIVG*--   267
Rhesus       : NITIKQHTV-TTTTKGENFTETDVKMMERVVEQMCITQYEKES--QAYY--QRGSSMVLFSSPPVILL--ISFLIFLIVG*--   260
Gibbon       : NITIKQHTV-TTTTKGENFTETDVKMMERVVEQMCITQYERES--QAYY--QRGSSMVLFSSPPVILL--ISFLIFLIVG*--   260
Macaque(S)   : NITIKQHTV-TTTTKGENFTETDVKMMERVVEQMCITQYEKES--QAYY--QRGSSMVLFSSPPVILL--ISFLIFLIVG*--   260
Macaque(C)   : NITIKQHTV-TTTTKGENFTETDVKMMERVVEQMCITQYEKES--QAYY--QRGSSMVLFSSPPVILL--ISFLIFLIVG*--   260
Macaque(J)   : NITIKQHTV-TTTTKGENFTETDVKMMERVVEQMCITQYEKES--QAYY--QRGSSMVLFSSPPVILL--ISFLIFLIVG*--   260
Macaque(P)   : NITIKQHTV-TTTTKGENFTETDVKMMERVVEQMCITQYEKES--QAYY--QRGSSMVLFSSPPVILL--ISFLIFLIVG*--   260
Marmoset     : NITIKQHTV-TTTTKGENFTETDVKMMERVVEQMCITQYEKES--QAYY--QRGSSMVLFSSPPVILL--ISFLIFLIVG*--   260
Hamadryas    : NITIKQHTV-TTTTKGENFTETDVKMMERVVEQMCITQYEKES--QAYY--QRGSSMVLFSSPPVILL--ISFLIFLIVG*--   259
Cercopithe.  : NITIKQHTV-TTTTKGENFTETDVKMMERVVEQMCITQYEKES--QAYY--QRGSSMVLFSSPPVILL--ISFLIFLIVG*--   260
Guereza      : NITIKQHTV-TTTTKGENFTETDVKMMERVVEQMCITQYEKES--QAYY--QRGSSMVLFSSPPVILL--ISFLIFLIVG*--   252
Capuchin     : NITIKQHTV-TTTTKGENFTETDVKMMERVVEQMCITQYEKES--QAYY--QRGSSMVLFSSPPVILL--ISFLIFLIVG*--   260
Francoisi    : NITIKQHTV-TTTTKGENFTETDVKMMERVVEQMCITQYEKES--QAYY--QRGSSMVFFSSPPVILL--ISFLIFLIVG*--   259
Siamang      : NITIKQHTV-TTTTKGENFTETDVKMMERVVEQMCITQYEKES--QAYY--QRGSSMVLFSSPPVILL--ISFLIFLIVG---   260
Mouse(RML)   : NITIKQHTV-TTTTKGEAFTETDVKMMERVVEQMCVTQYQKES--QAYYDGQRRSSSTVLFSSPPVILL--ISFLIFLIVG---   260
Mouse(Sh)    : NITIKQHTV-VTTTKGENFTETDVKMMERVVEQMCVTQYQKES--QAYYDGQRRSSSTVLFSSPPVILL--ISFLIFLIVG---   261
Mouse(Lg)    : NITIKQHTV-TTTTKGENFTETDVKMMERVVEQMCVTQYQKES--QAYYDGQRRSSSTVLFSSPPVILL--ISFLIFLIVG---   261
Hamster(C)   : NITIKQHTV-TTTTKGENFTETDVKMMERVVEQMCVTQYQKES--QAYYDGQRRSSA-VLFSSPPVILL--ISFLIFLIVG---   261
Cow          : NITVKEHTV-TTTTKGEAPTETDIKMMERVVEQMCITQYQRES--QAYY--QRGASVILFSSPPVILL--ISFLIFLIVG---   269
Sheep        : NITVKQHTV-TTTTKGENFTETDIKLMERVVEQMCITQYQRES--QAYY--QRGASVILFSSPPVILL--ISFLIFLIVG---   256
Antelope     : NITVKQHTV-TTTTKGENFTETDIKMMERVVEQMCITQYQRES--QAYY--QRGASVILFSSPPVILL--ISFLIFLIVG---   261
Kudu         : NITVKQHTV-TTTTKGENFTETDIKMMERVVEQMCITQYQRES--EAYY--QRGASVILFSPPPVILL--ISFLIFLIVG---   269
Goat         : NITVKQHTV-TTTTKGENFTETDVKMIERVVEQMCITQYQKEY--QAYY--QRGASVILFSSPPVILL--ISFLIFLIVG---   261
Pig          : NITVKQHTV-TTTTKGENFTETDVKMIERVVEQMCVTQYQQES--EAYA--QRGASAILFSPPPVILL--ISFLFLIVG---   262
Polecat      : NITVKQHTV-TTTTKGENFTETDMKIMERVVEQMCVTQYQKES--EAYY--QRGASAILFSPPPVILL--ISLLLLIVG---   262
Dog          : NITVKQHTV-TTTTKGENFTETDVKMMERVVEQMCVTQYQKES--QAYY--QRGASAILFSPPPVILL--ISLLLLIVG---   261
Rabbit       : NITVKQHTT-TTTTKGENFTETDIKIMERVVEQMCITQYQQES--QAAY--QRAAGVLLFSSPPVILL--ISFLIFLIVG---   259
Marsupial    : NITVKQHTV-TTTTKGENFTETDIKIMERVVEQMCITQYQAEY--EA--AAQRAYNMAFFSAPPVTLLFSFLIFLIVS---   264
Chicken      : NITVTEYSIGPAAKNTSEAVAAANQTEVEMENKVVTKVIREMCVQQYREYRLASGIQLHPADTWLAVLLLLTTLFAMH---   277
```

*Fig. 6 (continued)*

The present invention relates to prion proteins.

BIOLOGICAL MATERIALS AND METHODS USEFUL IN THE DIAGNOSIS AND TREATMENT OF DISEASES

The present invention relates to prion proteins.

Prions are infectious pathogens that differ from bacteria, fungi, parasites, viroids, and viruses, both with respect to their structure and with respect to the diseases that they cause. Molecular biological and structural studies of prions promise to open new vistas into fundamental mechanisms of cellular regulation and homeostasis not previously appreciated. Kuru, Creutzfeldt-Jakob disease (CJD), fatal familial insomnia (FFI) and Gerstmann-Sträussler-Scheinker syndrome (GSS) are all human neurodegenerative diseases that are caused by prions and are frequently transmissible to laboratory animals. Familial CJD and GSS are also genetic disorders. No effective therapy exists to prevent these fatal disorders[2].

In addition to the prion diseases of humans, disorders of animals are included in the group of known prion diseases. Scrapie of sheep and goats is the most studied of the prion diseases. Bovine spongiform encephalopathy (BSE) is thought to result from abnormal feeding practices. BSE threatens the beef industry of Great Britain and possibly other countries; the production of pharmaceuticals involving cattle is also of concern. Control of sheep scrapie in many countries is a persistent and vexing problem[2].

Since 1986, more than 170,000 cattle have developed BSE in Great Britain. Many investigators contend that BSE, often referred to as "mad cow disease", resulted from the feeding of dietary protein supplements derived from rendered sheep offal infected with scrapie to cattle, a practice banned since 1988. It is thought that BSE will disappear with the cessation of feeding rendered meat and bone meal, as has been the case in kuru of humans, confined to the Fore region of New Guinea and once the most common cause of death among women and children. Kuru has almost disappeared with the cessation of ritualistic cannibalism.

Prion diseases are associated with the accumulation of a conformational isomer ($PrP^{Sc}$) of host-derived prion protein ($PrP^{c}$) with an increase in its β-sheet content[1]. According to the protein-only hypothesis, $PrP^{Sc}$ is the principal or sole component of transmissible prions[2]. Although the structure of $PrP^{c}$ has been determined[3] and has been found to consist predominantly of α-helices, the insolubility of $PrP^{Sc}$, which is isolated from tissue in a highly aggregated state and which has a high β-sheet content, has precluded high-resolution structural analysis. Various workers have attempted to make forms of PrP which are intermediate between the normal ($PrP^{c}$) form and the abnormal, pathogenic form ($PrP^{Sc}$), having a predominantly β-sheet form therefore termed the β-form.

Hornemann & Glockshuber *PNAS* 95, 6010–6014 (1998)[8] describe a β-intermediate which is an unfolding intermediate of mouse PrP and contains predominantly β-sheet elements of secondary structure as opposed to α-helix. Swietnicki et al (1997) *J. Biol. Chem.* 272:44, October 31 pp27517–27520 describe an identical folding intermediate derived from human $PrP^{90-231}$. The mouse β-intermediate is derived from oxidised PrP which contains the native disulphide bond. The mouse PrP intermediate required urea (a denaturant) for stabilisation. The reference on page 6011 "Results" states that the mouse β-intermediate exhibits stability at pH 4.0 in the absence of denaturant; however this is based upon an equilibrium calculation. The free energy of folding (Table 1, page 6012) is approximated from a fit of the equation described in Materials and Methods (page 6011) to the data in FIG. 1A. From this an equilibrium constant can be calculated which describes the small proportion of molecules that will exist as the β-intermediate in the absence of denaturant. The proportion of molecules in this state is low (around 0.2%) and nothing can be said about their solubility in the absence of denaturant as they are not detectable. Indeed one would argue they are extremely unlikely to be soluble in the absence of denaturant because folding intermediates are structural states that are populated during rearrangement of a polypeptide chain from a random structure to a defined native conformation, or vice versa. They are characterised as having native-like secondary structure, few tertiary interactions, increased molecular volume, increased side chain mobility and exposed hydrophobic residues. These properties combined make them prone to aggregation and, as such, are generally insoluble in the absence of denaturants. Several references describe these properties in detail[18-23].

Moreover, the above calculation is dependent upon the transition being a genuine equilibrium, ie. fully reversible. If the transition is not reversible this analysis is invalid. We have performed similar experiments and have found that full reversibility is abolished at protein concentrations in excess of 1 mg/ml, with refolding yields <100%.

Zhang et al (1997) *Biochem* 36:12, 3543–3553 describe a β-sheet form of recombinant Syrian hamster PrP containing residues 90–231 which is formed by a method involving refolding at a pH of 6.5. It is clear from page 3548, second column and FIG. 7, that the β-form described is neither monomeric nor soluble in aqueous solution.

According to a first aspect the invention provides a method of making a β-form of a prion protein which has more β-sheet than α-helix structure, can exist as a monomer and can retain solubility in aqueous solution in the s absence of a denaturant, the method comprising:

- providing a reduced prion protein which does not include a disulphide bond and causing the conformation of the protein to change so that it adopts the β-form.

Preferably, the change in conformation is caused by exposure to conditions of acidic pH, preferably a pH of 5.5 or less, more preferably a pH of 4.8 or less and most preferably a pH of 4.0.

Skilled persons will appreciate that the β-sheet and α-helix structure can be shown by circular dichroism spectropolarimetry as described herein. While the native prion protein state is characterised by a strong α-helical signal, the β-form of the invention shows a shift to a conformation dominated by β-sheet. By "dominated" in this context we include the meaning that there is more β-sheet structure of the prion protein than α-helix structure.

By "exist as a monomer" we include the meaning that the β-form of the prion protein does not exist as an aggregate of two or more β-form prion proteins. Skilled persons will appreciate that analytical sedimentation studies can be used to determine whether or not a protein exists in solution as a monomer or as an aggregate of two or more proteins. A suitable technique is described in Zhang et al (1997) Biochem, 36:12, 3542–3553 (see page 3545–3546 passage entitled Analytical Sedimentation). The technique involves the use of an analytical ultracentrifuge (Beckman Optimat XL-A) equipped with a six channel cell, using ultraviolet absorption between 220 and 280 nm.

By "can retain solubility in the absence of a denaturant" we include the meaning that a significant proportion eg around 30% or more of the β-form remains in solution as a monomer after centrifugation at 100,000 g for 1 hour and preferably 150,000 g for 8–16 hours, most preferably at 200,000 g for 8–16 hours. The centrifugation may be carried out on a 2 mg/ml aqueous solution of the β-form prion protein comprising Na Acetate+10 mM Tris. HCl+pH 4.0 at 25° C. The structural characteristics of the remaining protein in solution can be determined by circular dichroism spectropolarimetry, for example.

Preferably, the β-form remains soluble without denaturant to a concentration of more than 1 mg/ml, more preferably at least 12 mg/ml, and especially more than 20 mg/ml.

It will of course be appreciated that the above requirement for the β-form to be capable of retaining solubility in the absence of the denaturant in no way limits the invention to methods or compositions which do not include a denaturant.

A β-form of a prion protein of the invention also comprises a prion protein which has at least 20% of its residues in β-sheet structure, more preferably at least 50% and most preferably 50 to 60% or more, as determined by CD spectropolarimetry.

A β-form of a prion protein of the invention also comprises a prion protein which is non-aggregated and exhibits partial resistance to proteinase K digestion.

A β-form of a prion protein of the invention also comprises a prion protein which is non-aggregated but is capable of forming an aggregated fibrous and/or amyloid form, preferably on exposure to a denaturant.

Preferably, a β-form of a prion protein of the invention also comprises a prion protein which is non-aggregated but is capable of forming a non-fibrillar aggregate on exposure to conditions of sufficient ionic strength. Preferably, the non-fibrillar aggregate is capable of forming a fibrillar structure.

By "conditions of sufficient ionic strength" we mean an ionic strength capable of converting the non-aggregated β-form to an aggregated form. For example, salt concentrations of 50 mM to 500 mM, especially 100 mM or more are sufficient to cause murine β-form prion protein to form a non-fibrillar aggregate. A particularly preferred salt concentration is 100–200, more preferably 150 mM eg NaCl or KCl.

A β-form of a prion protein of the invention also comprises a prion protein which is capable of interconverting between a β-form as defined herein and an α-form of a prion protein as described herein.

A β-form of a prion protein of the invention may exhibit one or more of the above properties.

In another aspect, the invention provides a method of obtaining non-aggregated β-form from a sample comprising partially digesting the sample with proteinase K.

It will be appreciated that by "prion protein" is included variants, fragments and fusions that have interactions or activities which are substantially the same as those of a full length prion protein sequence, but which may be more convenient to use, for example in an assay. A "variant" will have a region which has at least 70% (preferably 80, 90, 95 or 99%) sequence identity with the 91–231 region of native human PrP sequence described herein or the corresponding region in the PrP of other species as measured by the Bestfit Program of the Wisconsin-Sequence Analysis Package, version 8 for Unix. The percentage identity may be calculated by reference to a region of at least 50 amino acids (preferably at least 75, 100, 120 or 140) of the candidate variant molecule, and the most similar region of equivalent length in the native 91–231 region, allowing gaps of up to 5%.

The percent identity may be determined, for example, by comparing sequence information using the GAP computer program, version 6.0 described by Devereux et al. (*Nucl. Acids res.* 12:387, 1984) and available from the University of Wisconsin Genetics Computer Group (UWGCG). The GAP program utilizes the alignment method of Neddleman and Wunsch (*J. Mol. Biol.* 48:443, 1970), as revised by Smith and Waterman (*Adv. Appl. Math* 2.482. 1981). The preferred default parameters for the GAP program include: (1) a unary comparison matrix (containing a value of 1 for identities and 0 for non-identities) for nucleotides, and the weighted comparison matrix of Bribskov and Burgess, *Nucl. Acids Res.* 14:6745, 1986 as described by Schwarts and Dayhoff, eds, *Atlas of Protein Sequence and Structure, National Biomedical Research Foundation*, pp 353–358, 1979; (2) a penalty of 3.0 for each gap and an additional 0.10 penalty for each symbol in each gap; and (3) no penalty for end gaps.

Hybrid prion proteins comprising amino acid sequences from two or more different species also fall within the scope of the term "prion protein" used herein. Hybrid proteins comprising protein domains from different species can be produced using known recombinant DNA techniques, such as those described in WO93/20093 in relation to hybrid human/porcine factor VIII proteins.

A "fragment" comprises at least 50, preferably 75, 100, 120 or 130 amino acids of the native 91–231 sequence.

Such activities will include the abilities mentioned herein, such as the ability to be soluble without denaturant and may include the ability to raise antibodies and for use in screening compounds in accordance with the following aspects of the invention and the ability to form an aggregated fibrous and/or amyloid form especially a non-fibrillar aggregate which preferably comprises spherical particles having a diameter of from approx 10–20 nM which can be visualised by electron microscopy, when exposed to suitable conditions etc.

Preferably, the β-form of a prion protein exhibits partial resistance to digestion with proteinase K(PK).

By "partial resistance to digestion with proteinase K (PK)" we include the meaning that after incubation of 1 mg/ml of the protein in 10 mM NaAcetate+10 mM Tris. Acetate, pH 8.0 with 0.5 μg/ml PK (based on the total digestion reaction volume) at 37° C. for 30 mins some protein can be shown to be undigested when subjected to SDS-PAGE as described herein. Preferably, the majority of the protein is undigested.

Preferably, the β-form of the invention displays resistance to digestion at increased concentrations of PK eg 5 μg/ml PK or more.

The disease-related isoform of PrP, $PrP^{Sc}$, is distinguished biochemically from the normal cellular isoform of the protein, $PrP^{c}$, by its partial resistence to digestion with the enzyme proteinase K. We have now demonstrated that not only aggregated β-PrP is protease resistant but also that the soluble β-PrP monomer is also PK-resistant and to a level approximating to that seen with $PrP^{Sc}$. This is strong evidence to support the contention that β-PrP may be the precursor of $PrP^{Sc}$.

The novel β-form, or an aggregate of two or more β-forms, of the invention may be used to prepare antibodies which selectively recognise the β-form (whether aggregated or not) rather than the α-form or vice versa.

By "α-form" of a prion protein we include the meaning of a prion protein which has more α-helical than β-sheet structure. The α-form may also be characterised by sensitivity to degradation by proteinase K.

Any reductant and conditions which allow reduction can be used in the method of the invention as long as they do not cause irreversible modification to the polypeptide chain.

Reduction of a disulphide bond can be determined by Ellman's assay (Ellman, G. L., 1959, *Arch Biochem & Biophys*). Reduction of the disulphide bond preferably takes place before the pH is lowered. The acidic pH at which conformation change takes place may be approximately pH 5.5 or less, and preferably pH 4.8 or less, most preferably a pH of 4.0. Skilled persons will appreciate that any buffer that is effective around pH 4.0 can be used, such as 10 mM NaAcetate+10 mM Tris.Acetate.

Preferably, the β-form has substantially the same molecular volume (measured by size exclusion chromatography) as the native form of the prion protein.

In a second aspect, the invention provides a preparation of a β-form of a prion protein wherein at least 1% of the β-form can exist as a monomer and can retain solubility in aqueous solution in the absence of a denaturant. Preferably, the β-form is obtainable by a method according to the first aspect of the invention.

The invention also provides the above (soluble, undenatured) β-form of a prion protein for use in medicine, preferably in the prevention, treatment and/or diagnosis of a prion disease.

It will be appreciated that by virtue of properties such as its solubility, the β-form is amenable to high resolution structural analysis and so has particular utility for research into the mechanisms of prion disease especially prion replication. Such utility is not found in known insoluble forms of prion proteins.

The prion disease may be selected from one or more of the diseases affecting humans. Alternatively or additionally, the prion diseases are selected from one or more of the diseases which affect domestic farm animals such as cows, sheep and goats. Other prion diseases include transmissible mink encephalopathy; chronic wasting disease of mule deer and elk, bovine spongiform encephalopathy and, more recently, a whole series of new animal diseases that are thought to have arisen from their dietary exposure to the BSE agent. These include feline spongiform encephalopathy, affecting domestic cats and captive wild-cats (such as cheetahs, pumas, ocelots, tigers) and spongiform encephalopathies of captive exotic ungulates (including kudu, nyala, gemsbok, eland).

Preferably, the prion protein is selected from human, bovine or ovine prion proteins, more preferably human prion protein.

According to a third aspect of the invention there is provided a method of making an antibody against a prion protein having a β-form as defined in accordance with the earlier aspects of the invention, comprising administering said β-form to an animal and collecting and purifying the directly or indirectly resulting antibody. The antibody may be polyclonal, but is preferably monoclonal.

By "antibody" in accordance with the invention we include molecules which comprise or consists of antigen binding fragments of an antibody including Fab, Fv, ScFv and dAb. We also include agents which incorporate such fragments as portions for targetting prion molecules and/or cells or viruses which display such molecules.

According to this aspect of the invention, there is also provided a monoclonal antibody capable of distinguishing between the native α-form and the β-form of a prion protein as defined in accordance with earlier aspects of the invention or vice versa. Also provided is a hybridoma cell capable of producing such a monoclonal antibody.

In accordance with this aspect of the invention there is also provided an antibody for use in medicine, which antibody binds preferentially to the β-form of a prion protein rather than to the α-form of the prion protein or vice versa. Preferably, the antibody is for use in the manufacture of a composition for use in the prevention, treatment and/or diagnosis of a prion disease.

According to a fourth aspect of the invention there is provided a method of detecting the presence of a prion protein having a β-form as defined in accordance with the earlier aspects of the invention in a biological sample. The method preferably comprises providing an antibody preparation comprising an antibody which preferentially binds the β-form rather than the α-form and detecting whether the antibody binds β-form.

Conveniently, the antibody is directly or indirectly labelled by suitable means and its binding to the β-form is detected by detecting a label.

Preferably, the biological sample comprises or consists of a bodily fluid or tissue such as blood or blood derivative, ie a component such as plasma, lymphoid tissue (such as tonsils, appendices, lymph or spleen), cerebrospinal fluid faeces, urine, lymph or sputum. The biological sample may be a tissue sample eg a biopsy tissue sample.

It may be advantageous to introduce an anti-β-form antibody into one of the tissues mentioned above either to detect β-form or to remove β-form before it reaches the brain. Such anti-β-form antibodies are preferably antibodies which preferentially react with the β-form rather than the normal α-form of the prion protein.

By "preferentially" according to the various aspects of the invention we include the meaning that the ratio of α/β binding may be 45/55, 25/75, more preferably, 10/90, 5/95, 1/99 or substantially 0/100.

The invention also provides a method of detecting antibodies in a biological sample, which antibodies bind preferentially to a β-form of a prion protein rather than the α-form comprising exposing the β-form to the biological sample to permit binding of antibody to the β-form and detecting the binding of antibody to the β-form. Optionally, the β-form is immobilised before exposure to the sample.

The invention also provides a method of obtaining a β-form binding agent which binds preferentially to a β-form of a prion protein rather than an α-form comprising exposing the β-form to a sample to permit binding of agents to the β-form and optionally collecting the agent bound to the β-form. Optionally, the β-form is immobilised before exposure to the sample. Preferably, the binding agent is directly or indirectly labelled and its binding to the β-form is detected by detecting the label.

The invention also provides a kit useful for diagnosing a prion disease from a biological sample comprising a binding agent, preferably an antibody, which is capable of preferentially binding the β-form rather than the α-form, or a β-form of a prion protein which binds said binding agent; and means for detecting binding of the binding agent to the β-form. The binding agent or β-form being coupled optionally to an inert support. Preferably, the means for detecting binding comprises a radioactive, enzymic or fluorescent label.

The invention also provides an in vitro method for diagnosing a predisposition to, or the presence of, a prion disease comprising providing a reduced α-form of a prion protein, preferably at a pH of around 5.5 or less, preferably pH 4.8 or less, most preferably a pH of 4.0; comparing the amount or rate of formation of a β-form as defined herein in the presence and absence of a biological sample eg from a patient. Increased rate or amount of β-form formation is indicative of a predisposition to, or the presence of, a prion disease.

The invention also provides a method of treating a biological sample to remove a β-form of a prion protein comprising providing a binding agent which binds preferentially to the β-form of a prion protein rather than to the α-form of the prion protein, exposing the biological sample to the binding agent whereby a β-form of a prion protein can bind the binding agent and optionally collecting the treated biological sample. Preferably, the binding agent is immobilised before the exposure to the sample.

The invention also provides a method of diagnosing a predisposition to, or the presence of, a prion disease comprising providing a β-form of a prion protein; providing a biological sample; and exposing the solution to the sample and detecting the presence of an aggregation of the β-form, such an aggregation being indicative of predisposition to, or the presence of, a prion disease.

Preferably, the aggregation of the β-form is a non-fibrillar aggregate which preferably comprises spherical or irregularly shaped particles having a diameter of from 10–20 nm which can be visualised by electron microscopy.

The invention also provides the use of a β-form or a non-fibrillar aggregate thereof in the manufacture of a composition for use as a vaccine against a prion disease. A vaccine composition of the invention preferably comprises a β-form or a non-fibrillar aggregate thereof and an adjuvant.

According to a fifth aspect of the invention there is provided a method of identifying an agent that is capable of preventing, reducing and/or reversing the conversion of a prion protein to a β-form as defined above, the method comprising: providing a sample of a prion protein and comparing the amount of the β-form quantitatively or qualitatively in the presence and absence of a test agent.

In a sixth aspect of the invention, there is provided a method of identifying an agent that is capable of preventing or reducing the conversion of a prion protein from the β-form, as defined in accordance with earlier aspects of the invention, to an aggregated fibrous and/or amyloid form, especially a non-fibrillar aggregate mentioned above, the method comprising providing a solution containing the β-form and comparing qualitatively or quantitatively the amount of the aggregated and/or amyloid form produced in the presence and absence of a test agent.

Preferably, the amount of the aggregated and/or amyloid, especially non-fibrillar aggregate, form is measured using a spectrofluorimeter.

In a seventh aspect of the invention there is provided an agent which is identifiable by a method as defined in accordance with the fifth or sixth aspect of the invention.

In an eighth aspect the invention provides an agent capable of preventing, reducing and/or reversing the conversion of a prion protein from an α-form to a β-form as defined in accordance with earlier aspects of the invention.

In a ninth aspect the invention provides an agent capable of preventing or reducing the conversion of a β-form of a prion protein as defined in accordance with earlier aspects of the invention to an aggregated and/or amyloid , especially non-fibrillar aggregate, form.

The agents according to the seventh, eighth and ninth aspects of the invention may be a drug-like compound or lead compound for the development of a drug-like compound. Thus, the methods may be methods for identifying a drug-like compound or lead compound for the development of a drug-like compound that is capable of preventing, reducing and/or reversing the conversion of a prion protein to a β-form; and/or that is capable of preventing and/or reducing the conversion of the β-form to an aggregated and/or amyloid, especially non-fibrillar aggregate, form.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons molecular weight and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise, too toxic or has poor bioavailability) may provide a starting-point for the design of other compounds that may have more desirable characteristics.

The compounds identified in the methods of the invention may themselves be useful as a drug or they may represent lead compounds for the design and synthesis of more efficacious compounds.

In another aspect the invention provides an agent that comprises a binding agent portion which binds preferentially to the β-form of the prion protein rather than the α-form, and an effector portion which is capable of one or more of the following functions: (1) preventing, reducing and/or reversing the conversion of a prion protein to a β-form; (2) preventing or reducing the conversion of a prion protein from the β-form to an aggregated fibrous and/or amyloid, especially a non-fibrillar aggregate form; or (3) destroying a β-form of a prion protein and/or a cell or virus displaying such a protein.

Preferably, the binding agent portion comprise an antibody or a fragment thereof. Preferably the antibody or fragment thereof is made according to aspects of the present invention.

In one preferred embodiment the effector portion of an agent comprises a compound of the earlier aspects of the invention.

In another preferred embodiment the agent comprises an effector portion which is directly or indirectly cytotoxic.

By a "directly cytotoxic" portion we include a portion of an agent which is in itself toxic to the cell if it reaches, and preferably enters, the said cell.

By an "indirectly cytotoxic" portion we include a portion of an agent which can be converted into or produce a cytotoxic agent by the action of a further reagent, or which can convert a substantially non-toxic substance into a toxic substance. We also include a portion of an agent which can bind specifically to a compound which is directly or indirectly cytotoxic.

Non-limiting examples of cytotoxic portions include a drug, pro-drug, radionuclide, protein including an enzyme, antibody or any other therapeutically useful reagent, including cytokines such as tumour necrosis factor, interleukin-2 or interferon-γ.

Thus, the drug may be a cytotoxic chemical compound such as methotrexate, adriamicin, vinca alkaloids (vincristine, vinblastine, etoposide), daunorubicin or other intercalating agents. The protein may be ricin. The cytotoxic portion may comprise a highly radioactive atom, such iodine-131, rhenium-186, rhenium-188 or yttrium-90.

The enzyme, or enzymatic portion thereof, may be directly cytotoxic, such as DNaseI or RNase, or indirectly cytotoxic such as an enzyme which converts a substantially non-toxic pro-drug into a toxic form. The enzyme cytosine deaminase converts 5-fluorocytosine (5FC) to 5-fluorouracil (5FU) (Mullen et al (1922) *PNAS* 89, 33); the herpes simplex enzyme thymidine kinase sensitises cells to treatment with the antiviral agent ganciclovir (GCV) or aciclovir (Moolten (1986) *Cancer Res.* 46, 5276; Ezzedine et al (1991) *New Biol* 3, 608). The cytosine deaminase of any organism, for example *E. coli* or *Saccharomyces cerevisiae*, may be used. Examples of the construction of antibody-enzyme fusions are disclosed by Neuberger et al (1984) *Nature* 312, 604.

Other examples of pro-drug/enzyme combinations include those disclosed by Bagshawe et al (WO 88/07378), namely various alkylating agents and the Pseudomonas spp. CPG2 enzyme, and those disclosed by Epenetos & Rowlinson-Busza (WO 91/11201), namely cyanogenic pro-drugs (for example amygdalin) and plant-derived α-glucosidases. The nitroreductase/CB1954 system described by Bridgewater et al (1995) *Eur. J. Cancer* 31A, 2362–2370 is another example of an enzyme/prodrug combination suitable for use in the invention.

In a tenth aspect the invention provides an agent in accordance with the earlier aspects of the invention for use in medicine. Preferably, use of the aspects in the manufacture of a composition for use in the prevention, treatment and/or diagnosis of a prion disease, or for use as a research reagent.

In an eleventh aspect the invention provides a pharmaceutical composition comprising a pharmaceutically effective amount of an agent in accordance with the seventh, eighth and/or ninth aspects of the invention, together with a pharmaceutically acceptable diluent or carrier.

In a twelfth aspect the invention provides a method of preventing and/or treating a prion disease comprising administering to a subject an effective amount of an agent in accordance with the earlier aspects of the invention. By "effective amount" we include the meaning that sufficient quantities of the agent are provided to produce a desired pharmaceutical effect beneficial to the health of the recipient.

For a better understanding, the following non-limiting examples which embody certain aspects of the invention will now be described with reference to the following figures.

FIG. 1

(a) Secondary and tertiary structure of the two human PrP isoforms. The main graph shows CD spectra collected in the far UV region.

Oxidised human PrP at pH 8.0 is shown in open circles and displays a typically α-helical spectrum with 47% of amide residues involved in helical structure[17]. In contrast reduced human PrP at pH 4.0 displays a β-sheet spectrum, shown in open triangles. There is little or no helix present with up to 40% of amide residues adopting a β-sheet conformation[18]. The inset displays near UV CD spectra for oxidised human PrP pH 8.0 (open circles), reduced human PrP pH 4.0 (open triangles) and denatured human PrP (open squares). The oxidised protein clearly displays a high level of tertiary organisation in the aromatic region of the spectrum, whereas the denatured PrP lacks any distinct tertiary interactions. The reduced human PrP displays a level of tertiary organisation intermediate between native and denatured states.

(b) $^1$H NMR spectra of the upfield regions of the α- and β-forms of huPrP$^{91-231}$. Peaks upfield of 0.7 ppm are characteristic of strong tertiary interactions between methyl groups and aromatic rings found in folded, globular proteins.

(c) Expanded region of a $^1$H, $^{15}$N HSQC spectrum of the β-form of huPrP$^{91-231}$ showing its chemical shift dispersion, which is much reduced relative to the α-form (Hornemann S. and Glockshuber R., *J Mol Biol*, 261, 614–619 (1996)).

Figure 1B:
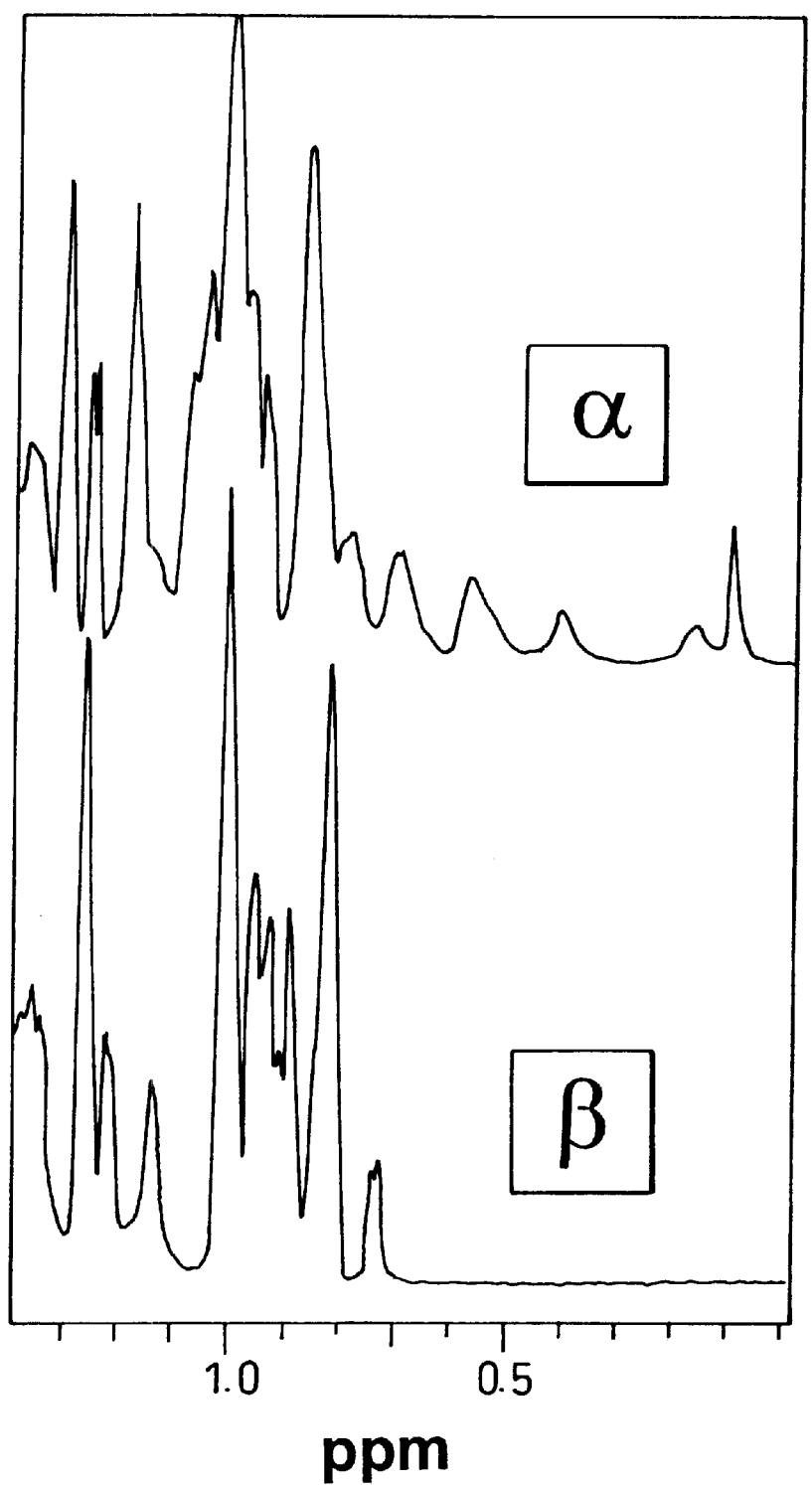
Figure 1C:
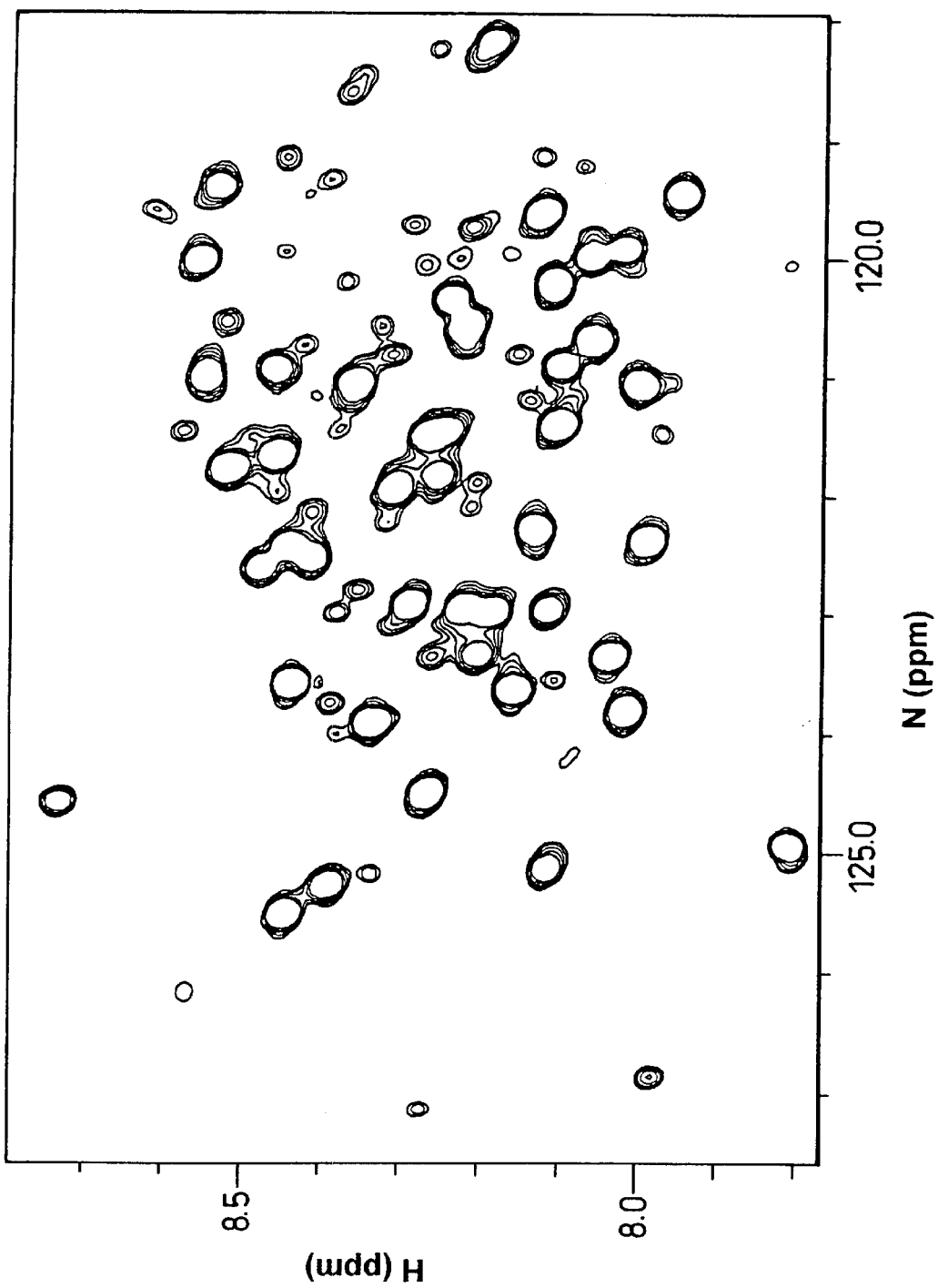

While the ID $^1$H-NMR spectrum of native human PrP$^{91-231}$ exhibits wide chemical shift dispersion characteristic of a fully folded globular protein, the 1D $^1$H and $^1$H $^{15}$N HSQC spectra of the β-form of PrP exhibit considerably less chemical shift dispersion (FIG. 1*b,c*). This lack of dispersion is characteristic of the loss of fixed side chain interactions, which, in conjunction with the aromatic CD results, suggests some similarities with molten globule states. In addition, proton and nitrogen line-widths of the β-form (FIG. 1*c*) are comparable to those observed in the folded and unfolded regions of the α-PrP conformation indicating that the β-form is monomeric at the extremely high concentrations required for NMR, thus confirming the gel-filtration results. The mobile unstructured regions of β-PrP have been assigned from the sharpness and height of the peaks. We find that residues 91–126 and 229–230 are mobile in β-PrP, moreover, this is the same region that is unstructured in the α-PrP conformation. Hence, the rearrangement from α-helix to β-sheet must occur within the structured region of the cellular conformation.

FIG. 2

Determination of the apparent molecular weight of PrP by size exclusion chromatography.

(a) Elution profile of molecular weight standards used to construct a calibration curve of molecular weight versus elution time (not shown). (b) Oxidised human PrP pH 8.0 in the alpha form elutes with an apparent molecular weight of 18 kDa. This excess weight (calculated mass is 16248 kDa) is due to the large molecular volume of PrP resulting from the dispersed secondary structure elements. (c) Reduced human PrP pH 4.0 in the β-form also elutes as a monomer with an apparent molecular weight of 18 kDa. (d) Oxidised human PrP at pH 4.0 partially denatured with 1M GuHCl. Addition of 1M GuHCl to oxidised human PrP at pH 4.0 results in aggregation and precipitation. Clarified supernatant contains a denatured form of PrP with an increased molecular volume corresponding to an apparent molecular weight of 40 kDa.

FIG. 3

β-PrP is more prone to form high molecular weight aggregates than α-PrP. Right angle light scattering of a 1 mg/ml solution of α-PrP (open circles) shows there are no high molecular weight aggregates formed upon addition of GuHCl. In contrast β-PrP, which is highly soluble in aqueous buffer alone, readily forms high molecular weight aggregates upon the addition of low concentration of GuHCl (open triangles). Maximum precipitation occurs at 0.4 M GuHCl, with subsequent re-dissolution of aggregates at higher concentrations of denaturant.

FIG. 4

β-PrP aggregates self-assemble into fibrils. The protein aggregates appear in two forms by negative stain electron microscopy. (A) The most common form is small (about 10 nm diameter) irregularly shaped and is seen in all samples. (B) The other aggregation form is fibrils which are increasingly prevalent the longer the sample is incubated. These fibres can be seen to intertwine, again a phenomenon that increases with time. Scale bars shown in white represent a length of 200 nm. In order to comply with safety regulations governing the handling of prion protein, electron microscopy was performed on mouse PrP$^{91-231}$ treated in an identical manner to the human protein.

β-PrP, at a concentration of 0.27 mg/ml in 20 mM sodium acetate pH4, was treated with 1/9 volumes of a 5M stock of GuHCl to give a final protein and denaturant concentrations of 0.25 mg/ml and 0.5 M respectively. The procedure for staining the protein is as follows. A dilute solution of PrP (~2 μl) is dropped onto the grid and the molecules adhere to the carbon film. Bonding to the surface prevents interactions between protein molecules. The sample is then flooded with 2% uranyl acetate w/v which coats the carbon surface and any particles stuck to it. The excess is blotted off leaving a thin film. This procedure seldom, if ever, leads to aggregation owing to the initial adherence to the grid surface. In our hands, when doing extensive single molecule work, we have not seen aggregation phenomena using this method. Further, when the PrP molecule is initially laid down the particles are small and circular and only produce fibrils after several hours. If the laying down process caused the aggregation we would not see this time-dependent behaviour.

FIG. 5

β-Prp displays partial PK resistance in monomeric and aggregated states. α-PrP is sensitive to PK digestion and is completely digested at 0.5 μg/ml PK. The concentrations of PK indicated are the final concentrations in the digestion reactions.

Using identical conditions for digestion in which β-PrP remains soluble and monomeric (data not shown), soluble β-PrP has partial resistance to proteinase K with the majority of protein undigested at 0.5 μg/ml. Aggregated β-PrP possesses increased resistance to PK digestion with some protein surviving intact at 5 μg/ml PK. The concentrations of PK indicated are the final concentrations in the digestion reactions. Although β-PrP reverts to α-PrP at pH8.0 this process requires several days for completion. Within the timescale of PK digestion the protein remains as β-PrP.

FIG. 6

Known prion protein sequences from other mammalian species, using the single letter code for amino acids as follows:

A=Ala; D=Asp; E=Glu, F=Phe; K=Lys; L=Leu; M=Met; N=Asn; P=Pro; Q=Gly; R=Arg; S=Ser; T=Thr; and V=Val.

Such information is available from databases such as EMBL, Genbank, Swis-Prot, Brookhaven.

METHODS

1. Purification of Human PrP

Plasmid Design and Protein Expression

The open reading frame of the human PrP gene was amplified by PCR using oligonucleotide primers designed to create an unique N-terminal BamHI site and C-terminal HindIII site for directional cloning of the fragment into the expression vector pTrcHisB (Invitrogen Corp.). The primer corresponding to the N-terminal region of PRNP to be expressed was designed to mutate a glycine at codon 90 to methionine, with the C-terminal primer replacing a methionine residue at 232 to a stop codon.

Human PrP Open Reading Frame: SEQ ID NO. 35

```
  1 ATGGCGAACC TTGGCTGCTG GATGCTGGTT CTCTTTGTGG CCACATGGAG
 51 TGACCTGGGC CTCTGCAAGA AGCGCCCGAA GCCTGGAGGA TGGAACACTG
101 GGGGCAGCCG ATACCCGGGG CAGGGCAGCC CTGGAGGCAA CCGCTACCCA
151 CCTCAGGGCG GTGGTGGCTG GGGGCAGCCT CATGGTGGTG GCTGGGGGCA
201 GCCTCATGGT GGTGGCTGGG GGCAGCCCCA TGGTGGTGGC TGGGGACAGC
251 CTCATGGTGG TGGCTGGGGT CAAGGAGGTG GCACCCACAG TCAGTGGAAC
301 AAGCCGAGTA AGCCAAAAAC CAACATGAAG CACATGGCTG GTGCTGCAGC
351 AGCTGGGGCA GTGGTGGGGG GCCTTGGCGG CTACATGCTG GGAAGTGCCA
401 TGAGCAGGCC CATCATACAT TTCGGCAGTG ACTATGAGGA CCGTTACTAT
451 CGTGAAAACA TGCACCGTTA CCCCAACCAA GTGTACTACA GGCCCATGGA
501 TGAGTACAGC AACCAGAACA ACTTTGTGCA CGACTGCGTC AATATCACAA
551 TCAAGCAGCA CACGGTCACC ACAACCACCA AGGGGGAGAA CTTCACCGAG
601 ACCGACGTTA AGATGATGGA GCGCGTGGTT GAGCAGATGT GTATCACCCA
651 GTACGAGAGG GAATCTCAGG CCTATTACCA GAGAGGATCG AGCATGGTCC
701 TCTTCTCCTC TCCACCTGTG ATCCTCCTGA TCTCTTTCCT CATCTTCCTG
751 ATAGTGGGAT GA
```

N-terminal Sense Oligo: SEQ ID NO. 36
5'-TTTG GAT CCG ATG CAA GGA GGT GGC ACC CAC-3'

C-terminal Antisense Obligo: SEQ ID NO. 37
5'-CAA GAA GCT TTC AGC TCG ATC CTC TCT GG-3'

The ligated pTrcHisB/PRNP construct was used to transform the E. coli host strain BL21 (DE3) (Novagen), genotype F' ompT hsdS$_B$ (r$_B^-$m$_B^-$) gal dcm (DE3) which was then plated onto Luria-Bertoni (LB) agar plates containing 100 μg/ml carbenicillin. Following growth overnight at 37° C. single colonies were picked and used to inoculate 10×10 ml of LB broth containing 100 μg/ml carbenicillin. This culture was grown overnight at 37° C. with vigorous shaking. The 10 ml cultures were used as inocula for 10×1 litre of LB broth containing 100 μg/ml carbenicillin which had been pre-warmed to 37° C. Growth at 37° C. with vigorous shaking was allowed to progress until the culture reached an OD$_{600}$ of 0.6. Expression was then induced by addition of isopropyl-β-D-galactopyranoside to a final concentration of 1 mM and the culture resupplemented with carbenicillin to a level of 100 μg/ml. Following 4 hours of induced growth the cells were harvested by centrifugation at 8,500 rpm for 10 minutes.

Extraction, Refolding and Purification of Recombinant Human PrP

The cell pellet was resuspended in 50 ml of lysis buffer (50 mM Tris. Cl pH 8.0, 200 mM NaCl, 0.1% Triton X100, 10 μg/ml DNase 1, 10 μg/ml lysozyme) and disrupted by sonication in 1 minute bursts for a total of 5 minutes. Centrifugation at 9,600 rpm for 30 minutes pelleted all the insoluble material and the supernatant was discarded. The pellet was then washed twice by resuspension in 50 ml of lysis buffer with centrifugation at 7,500 rpm for 5 minutes between each wash. Solubilisation of protein in the pellet was performed by resuspension in 50 ml of 50 mM Tris. Cl, 6M GuHCl, 100 mM DTT pH 8.0. Cell debris and insoluble material was removed by centrifugation at 9,600 rpm for 30 minutes. The supernatant was clarified by passage through a 0.2 μm filter and loaded onto a 20 ml Ni-NTA-Sepharose (Quiagen) column pre-equilibrated with 50 mM Tris. Cl, 6M GuHCl pH 8.0.

After washing the column with the above buffer, bound protein was eluted with a 15 column volume linear gradient of 0 mM to 300 mM imidazole in loading buffer. Recombinant PrP eluted at 185 mM imidazole. Eluted fractions were pooled and oxidation of disulphides was achieved by vigorous stirring in the presence of 1 μM $CuSO_4$ and dissolved atmospheric oxygen for 16 hours. PrP containing oxidised disulphides was separated from reduced protein using reverse phase chromatography on an RP304-C4 column. The protein was loaded in 50 mM Tris.Cl, 6M GuHCl pH 8.0, washed with $ddH_2O$+0.1% trifluoroacetic acid (TFA) and eluted with a linear gradient of 15% to 60% acetonitrile+0.09% TFA. Human PrP emerged as two major peaks; oxidised protein at 40% acetonitrile and a second peak containing reduced PrP eluted at 45% acetonitrile. The oxidised peak fractions were pooled and neutralised by the addition of 1M Tris.Cl pH 8.0 to a final concentration of 100 mM and saturated ammonium sulphate added to a final concentration of 70%. Precipitated PrP accumulated at the interface between organic and aqueous phases and was removed to a separate container. The protein was solubilised in a minimal volume of 50 mM Tris.Cl, 6M GuHCl pH 8.0 and then diluted rapidly to a protein concentration of 1 mg/ml and dialysed for 16 hours against 50 mM Tris.Cl pH 8.0 with a buffer change after 8 hours. Following dialysis the N-terminal fusion peptide was removed by addition of enterokinase at 1unit/3 mg protein. Cleavage was allowed to occur at 37° C. for 14 hours and terminated by the addition of "protease complete" (Boehringer Mannheim Corp).

Final purification was carried out by applying the protein material to a 10 ml S-Sepharose FastFlow column equilibrated with 25 mM Tris.Cl pH 7.0 and following a 5 column volume wash with the same buffer, protein was eluted with a 10 column volume linear gradient of 0 mM to 300 mM NaCl. Recombinant PrP lacking the N-terminal fusion peptide eluted at 150 mM whilst uncleaved material remained bound until 250 mM NaCl. Eluted fractions were concentrated in an Amicon cell with a 10 kDa cut off membrane and then dialysed overnight against 25 mM Tris.Cl pH 7.0, 0.02% NaAzide containing a small amount of activated charcoal. Sucrose was added to 5% w/v and the protein snap frozen in liquid nitrogen for long term storage at −80° C.

Recombinant human PrP in the oxidised α-form was purified as described above and dialysed into 10 mM NaAcetate+10 mM Tris.HCl pH 8.0. To convert this material to the β-form the protein was reduced and denatured in 100 mM DTT in 6M GuHCl+10 mM NaAcetate+10 mM Tris.HCl pH 8.0 for 16 hrs. The protein was refolded by dialysis against 10 mM NaAcetate+10 mM Tris.HCl+1 mM DTT pH4.0 and precipitated material removed by centrifugation at 150,000 g for 8 hrs. Protein concentration was determined by UV absorption using a calculated molar extinction coefficient of 19632 $M^{-1}$ $cm^{-1}$ at 280 nm.

2. Determination of Aggregation State of PrP by Gel Filtration

A Bio-Sil 125-5 size exclusion column (BioRad) equilibrated with the appropriate buffer at a flow rate of 1 ml/min producing a back pressure of 900 psi. A 20 μl (360 μg) aliquot of molecular weight standards (BioRad) containing markers of 670 kDa, 158 kDa, 44 kDa, 17 kDa and 1.35 kDa was loaded onto the column equilibrated with 10 mM NaAcetate+10 mM Tris.HCl+50 mM NaCl. The markers were eluted with 2 column volumes (30 ml) of the same buffer and used to construct a calibration curve for the column. The α-PrP was loaded in a volume of 100 μl (200 μg) and eluted with 30 mls of 10 mM NaAcetate+10 mM Tris.HCl+50 mM NaCl pH 8.0. β-PrP was loaded in volume of 100 μl (200 μg) and eluted with 30 mls of Na Acetate+100 mM Tris.HCl+50 mM NaCl pH 4.0.

3. Circular Dichroism Spectropolarimetry

For circular dichroism (CD) measurements 62.5 μM protein was incubated at 10 mM NaAcetate+10 mM Tris.HCl at either pH 8.0 (α-Prp) or pH 4.0 (β-PrP) and molecular ellipticity ([θ], degree $M^{-1}$ $cm^{-1}$ was recorded in the far UV range between 190 nm and 250 nm, using a xenon light source in a Jobin-Yvon CD6 spectrometer (cell path length 0.01 cm, slit width 1.0 nm; 2 nm bandwidth, integration time 20 sec). Near UV CD spectra were recorded between 250 nm and 310 nm using 62.5 μM protein in a 10 nm pathlength cuvette with a slit width of 1.0 nm (2 nm bandwidth, integration time 20 sec). All data were recorded at 25° C.

4. NMR Spectroscopy

NMR spectra. shown were acquired at 293 K on a Bruker DRX-500 spectrometer. Sample conditions were as follows, α-form: 1 mM human $PrP^{91-231}$ in 20 mM sodium acetate-$d_3$, 2 mM sodium azide, (10% $D_2O$ (v/v)) pH 5.55; β-form: 0.75 mM human $PrP^{91-231}$ in 20 mM sodium acetate-$d_3$, 2 mM sodium azide, (10% $D_2O$ (v/v)) pH 4. 1D $^1H$ NMR spectra were acquired with an acquisition time of 656 ms; $^1H$, $^{15}N$ HSQC spectra with acquisition times of 328 ms and 168 ms in the direct and indirect dimentions respectively. NMR data were processed using Felix 97 (Molecular Simulations Inc). Proton chemical shifts were referenced indirectly to TSP via the water signal.

5. Aggregation of β-PrP Observed by Right Angle Light Scattering

Either oxidised human PrP pH 8.0 was diluted to 1 mg/ml in 2 mls of 10 mM NaAcetate+10 mM Tris.HCl pH 8.0, or reduced human PrP pH 4.0 was diluted to 1 mg/ml in 2 mls of the same buffer at pH 4.0. The presence of aggregated material was monitored by right angle light scattering in a Schimadzu RF-5301 PC spectrofluorimeter with both excitation and emission monochromators set to slit width of 3 nm. 30 μl aliquots of 6M GuHCl were added and the solution allowed to equilibrate for a few minutes before each reading was taken. All data were collected at 25° C.

6. Electron Microscopy

Reduced protein refolded at pH 4.0 to form β-sheet structure was examined using electron microscopy (EM). The specimens were prepared using standard negative stain procedures. Three microlitres of protein solution at a concentration of 0.25 mg/ml were pipetted onto carbon films mounted on copper EM grids. After one minute the grids were washed with 80 microlitres of aqueous 2% uranyl acetate. The stain was left for approximately 10 sec before being blotted with filter paper. The grids were then inserted into a JEOL 1200 transmission electron microscope. Electron micrographs at approximately 1 micron underfocus were recorded on Kodak SO-163 film under normal exposure conditions at 40,000× magnification (calibrated against a grating) at 120 KeV. The defocus of the negatives was confirmed by optical diffractometry.

7. Digestion with Proteinase K

Both α-PrP and β-PrP as a monomer and aggregate were subjected to digestion with varying concentrations of proteinase K (BDH) at 37° C. for 1 hr. Protein was digested at a concentration of 1 m/ml in 10 mM NaAcetate+10 mM Tris. Acetate pH 8.0. Digestion was terminated by the addition of Pefablock (Boehringer Mannheim Corp.) to a final concentration of 1 mM. Following the adition of Pefabloc samples were heated to 100° C. for 5 mins in the presence of SDS loading buffer. Aliquots of 20 μl were subjected to SDS-PAGE and the gels stained with Coomassie brilliant blue.

Here we demonstrate the reversible interconversion of recombinant human PrP between the native α-form, characteristic of $PrP^c$, and a similarly compact, highly soluble, monomeric form rich in β-structure which is stable in aqueous solution. Such an interconversion of a protein chain between two, discrete, monomeric backbone topologies is unprecedented. We further show that this soluble β-form (β-PrP) is a direct precursor of fibrillar structures that are closely similar to those isolated from diseased brains. The conversion of $PrP^c$ to β-PRP in suitable cellular compartments, and its subsequent stabilisation by intermolecular associated, provides a possible molecular mechanism for prion propagation.

Human $PrP^{91-231}$ was expressed to high levels in E. coli as a protein aggregate and solubilised by extraction with 6 M guanidinium chloride and reducing agent. Subsequent purification, removal of denaturant and oxidation yielded a highly soluble, monomeric protein with a single intact disulphide bridge. Analysis of this refolded material by circular dichroism (CD) spectropolarimetry revealed a structure rich in a α-helical content (47%) with little β-sheet (18%) (FIG. 1a legend). One-dimensional $^1$H nuclear magnetic resonance (NMR) spectra (FIG. 1b) and two-dimensional $^1$H-$^{15}$N correlation NMR spectra (data not shown) of this material show it to be conformationally similar to the previously determined mouse and hamster prion proteins[3,4], and a previously characterised human $Prp^{91-231}$ construct[5].

Figure 2:
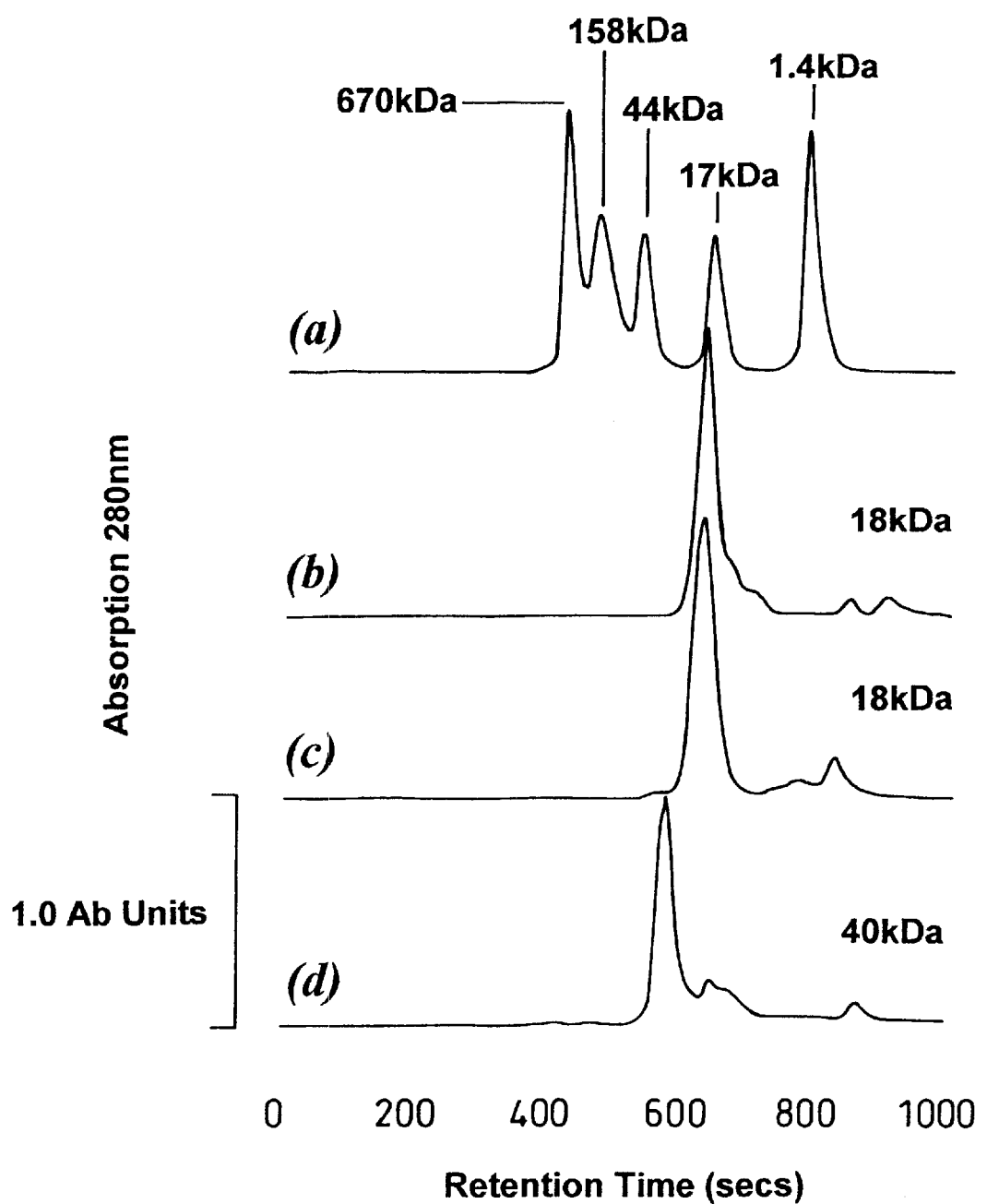

In common with mouse PrP[6], human $PrP^{91-231}$ folds and unfolds through a freely reversible transition (ΔG=−5.6 Kcal./mol) between the fully native state and a random coil, with no detectable equilibrium intermediates. However, reduction of the disulphide bond in human $Prp^{91-231}$, and lowering the pH to 4.0 in a dilute acetate buffer in the absence of additives, generates a highly soluble protein which can be concentrated to at least 12 mg/ml. When the reduced protein is subjected to gel filtration, it elutes as a monomeric species (FIG. 2). The CD signal in the amide region of the spectrum (FIG. 1a) shows that this highly soluble reduced species adopts a radically different conformation from $PrP^c$. While the native state is characterised by a strong α-helical signal, the reduced form shows the shift to a conformation dominated by β-sheet. This constitutes the first observation of a soluble monomeric β-form of the prion protein which opens up the opportunity for biophysical study.

This type of secondary structural transition has been well-documented in proteins that undergo a switch from a soluble monomeric state to an aggregated fibrous and/or amyloid form in which β-structure is stabilised by intermolecular interactions[7]. However, it is unprecedented for a protein to undergo such a β-sheet conversion while remaining in a monomeric state at high protein concentrations and in the absence of denaturants. This is in contrast to the β-intermediate of mouse $PrP^{121-123}$ [8] which required the presence of denaturant for stabilisation. A similar folding intermediate of human α-$PrP^{91-231}$ exists but is poorly soluble. Clarified material has an increased apparent molecular weight of 40 kDa (FIG. 2), indicative of tertiary disorder and expanded molecular volume. Using the amide CD signal alone, it is uncertain whether the non-native compact conformation of human β-$PrP^{91-231}$ is sufficiently condensed to have immobilised side-chains characteristic of the native state of orthodox, globular proteins. However, the aromatic region of CD spectra contains signals from aromatic side-chains in asymmetric environments. Compared to the native, oxidised molecule, the β-form retains a signal from aromatic residues but the intensity is diminished (FIG. 1a). This result indicates that packed tertiary interactions present in $PrP^c$ have been weakened, but not lost, in the β-conformation. Similarly, gel filtration of the reduced state reveals that is has, within the resolution of the technique, the same level of compactness as the $PrP^c$ conformation (FIG. 2).

From the above measurement it is not clear whether the reduced form of the protein is classifiable as a molten globule or whether it is better described as an alternative, fully folded conformation with well-defined tertiary interactions between side-chains. The term 'molten globule' was first used to describe distinct states adopted by some protein molecules when exposed to mildly denaturing conditions such as moderate concentrations of chaotropic agents (urea or guanidinium chloride) or acidic pH[9]. The chief signatures of the molten globule state are a well organised pattern of native-like backbone (secondary) structure with disordered side-chains and poorly defined tertiary interactions[10]. Originally, they were defined as equilibrium states but as more information became available on the behaviour of transiently populated, kinetic intermediates in folding reactions, often referred to as 'I-states' the definition has become blurred. This uncertainty is explained by the fact that I-states and molten globules have the above features in common, except that the former, kinetic intermediates are populated in native conditions. Despite this distinction, it has been shown for a number of proteins that molten globule states and I-states are experimentally indistinguishable[11]. Moreover, because the I-state can be considered to be the denatured conformation in physiological conditions, it has attracted much attention with the context of cellular processes such as chaperone-assisted folding, protein transport between cellular compartments and amyloidosis.

Due to exposure of normally buried non-polar residues, it is rare for non-native states to show high solubility in the absence of denaturants. However, the availability of the β-form of PrP as a monomeric species at a concentration of 0.75 mM provided the opportunity of examining its physical properties using NMR. While the 1D $^1$H-NMR spectrum of native human $PrP^{91-231}$ exhibits wide chemical shift dispersion characteristic of a fully folded globular protein, the spectrum of the β-form of PrP exhibits considerably less chemical shift dispersion. This lack of dispersion is characteristic of the loss of fixed side chain interactions, a defining feature of molten globule states[12-14]. However, residual dispersion appears to be greater than that expected for a fully unfolded protein (FIG. 1b), implying some degree of tertiary packing in the β-form. This finding is consistent with the reduced but significant CD signal for the β-form in the aromatic region of the spectrum (FIG. 1a). Therefore coupled with the amide CD data (FIG. 1b), the NMR chemical shift data points to the β-form being predominantly molten globular in nature. In addition, proton line-widths of the β-form are comparable to those observed in the native $PrP^c$ conformation indicating that it is monomeric at the extremely high concentrations required for NMR and confirming the gel-filtration results.

The switch from α-to-β conformation is reversible. When the reduced β-form is exposed to a higher pH (8.0), the native α-conformation is restored. However, the rates of inter-conversion, in either direction, are extremely slow, requiring a period of days for completion (data not shown). This high kinetic barrier, however, can be side-stepped by fully denaturing and refolding at the appropriate pH to generate either isoform.

By "fully denaturing" we include the meaning that there is no detectable secondary or tertiary structure ie the protein forms a "random coil". Such denaturation can be determined by Circular Dichroism and/or NMR spectroscopy as described herein and can be achieved, for example, by maintaining the prion protein in 100 mM DTT in 6M GuHCl+10 mM NaAcetate+10 mM NaAcetate+10 mM Tris. HCl pH 8.0 for 16 hours.

Figure 3:
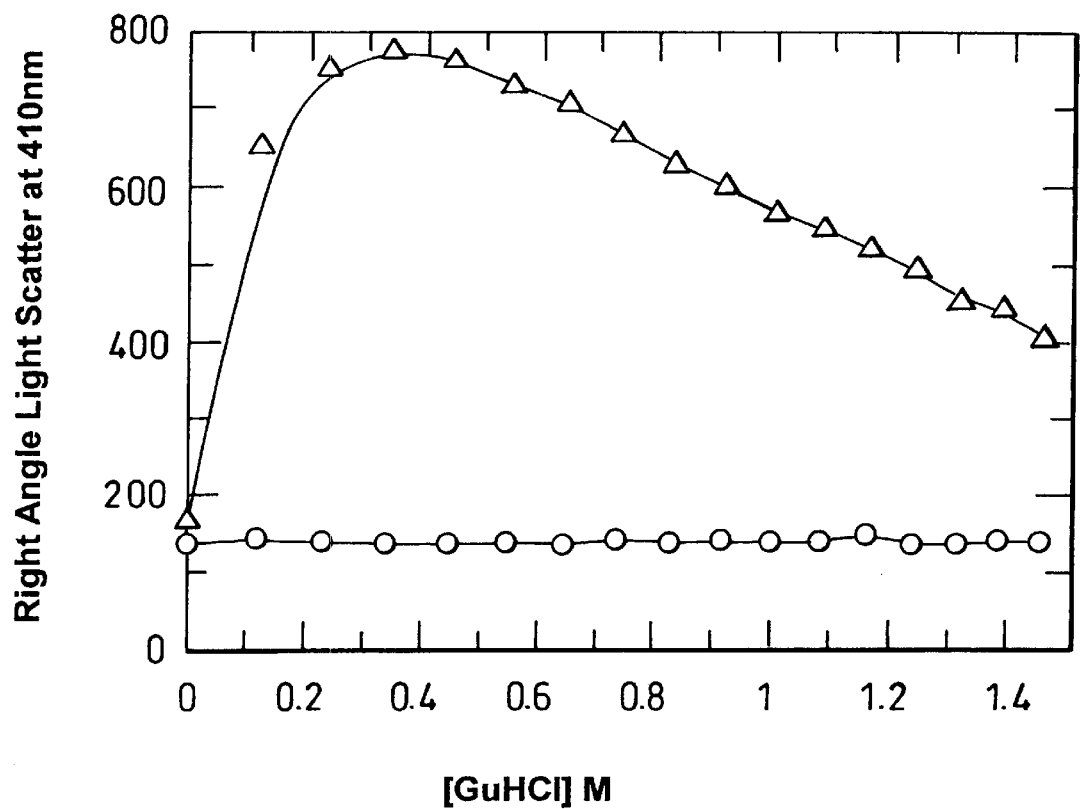
Figure 4:
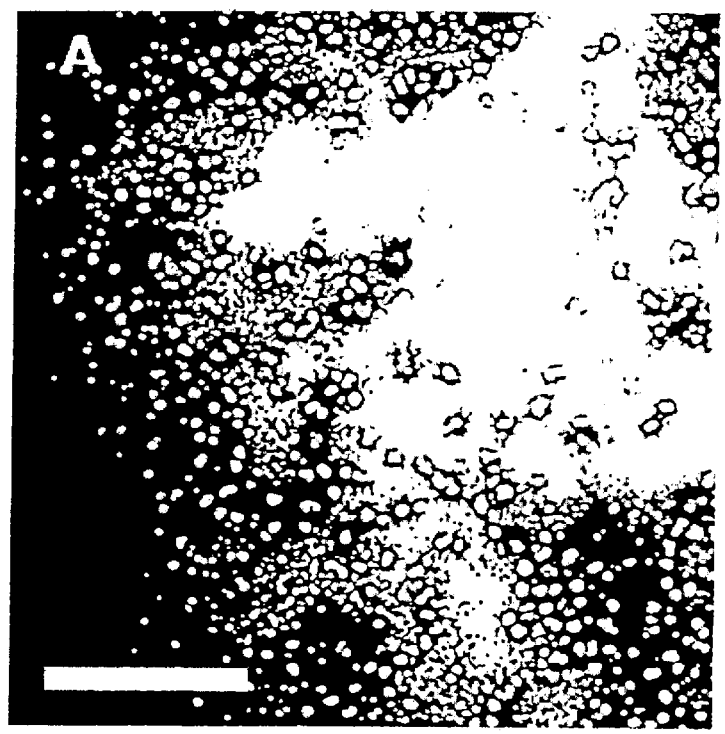
Figure 4:
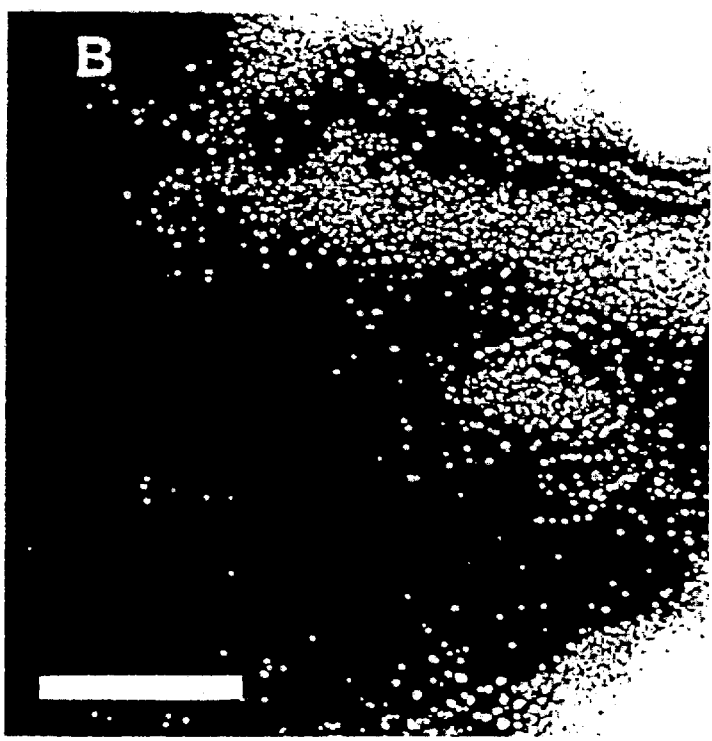

Solubility of the two isoforms is not equivalent. The α-form of PrP can be titrated with the denaturant guanidine hydrochloride (GuHCl) in order to determine equilibrium parameters for the folding pathway (data not shown). However, while the β-form of PrP is also highly soluble in aqueous buffers, titration with GuHCl leads to intermolecular associations resulting in a visible precipitate (FIG. 3). This material, when examined at high magnification, is initially composed of irregular spherical particles (FIG. 4a) which associate over several hours to form fibrils (FIG. 4b), very similar in appearance to those identified in diseased tissue.

Figure 5:
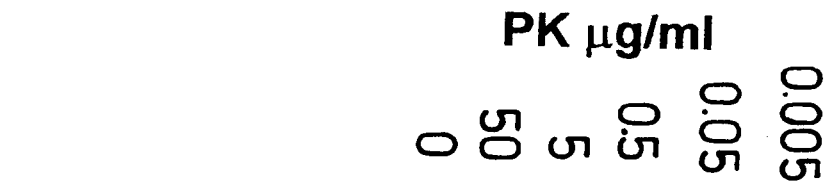
Figure 5:
Figure 5:
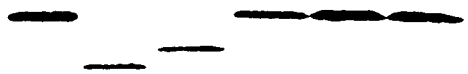
Figure 5:
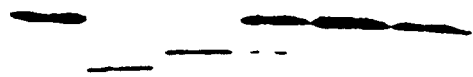

$PrP^{Sc}$ is characterised by its partial resistance to digestion with proteinase K (PK). As with native $PrP^c$, α-PrP is extremely sensitive to digestion with PK (FIG. 5). However, β-PrP shows marked protease resistance. This PK resistance is a function of the structural re-organisation of the monomeric β-form, with only a moderate further increase associated with aggregation (FIG. 5). The different patterns of proteolytic cleavage fragments seen on PK digestion of α-PrP and β-PrP provide further evidence of a major conformational re-arrangement in β-PrP. In marked contrast, the partially structured β-sheet conformation of reduced hamster $PrP^{90-231}$ reported by Mehlhorn at al[18] and Zhang et al (1997) Biochem, 36:12, 3542–3553[19] is fully sensitive to PK digestion.

Unusually for a protein with a predominantly helical fold, the majority of residues in $PrP^{91-231}$ have a preference for β-conformation (55% of non-glycine/proline residues). In view of this property, it is possible that the PrP molecule is delicately balanced between radically different folds with a high energy barrier between them; one dictated by local structural propensity (the β-conformation) and one requiring the precise docking of side-chains (the native α-conformation). Such a balance would be influenced by mutations causing inherited human prion diseases[15]. It is also worthy of note that individuals homozygous for valine at polymorphic 129 of human PrP (where either methionine or valine can be encoded) are more susceptible to iatrogenic $CJD^{16}$, and valine has a much higher β-propensity than does methionine. Our results lend support to such a hypothesis by showing that the molecule is capable of slow inter-conversion between a native a and a non-native β conformation. Furthermore, we demonstrate that the β-form can be locked by intermolecular association, thus supplying a plausible mechanism of propagation of a rare conformational state. It is possible that the $PrP^c$ to β-PrP conversion we describe here, caused by reduction and mild acidification, is relevant to the conditions that $PrP^c$ would encounter within the cell, following its internalisation during re-cycling. Such a mechanism could underlie prion propagation, and account for the transmitted, sporadic and inherited aetiologies of prion disease. Initiation of a pathogenic self-propagating conversion reaction, with accumulation of aggregated β-PrP, may be induced by exposure to a 'seed' of aggregated β-PrP following prion inoculation, or as a rare stochastic conformational change, or as an inevitable consequence of expression of a pathogenic $PrP^c$ mutant which is predisposed to form β-PrP.

8. Antibody Production Method

Methods for purification of antigens and antibodies are described in Scopes, R. K. (1993) *Protein purification* 3rd Edition. Publisher—Springer Verlag. ISBN 0-387-94072-3 and 3-540-94072-3. The disclosure of that reference, especially chapters 7 and 9, is incorporated herein by reference.

Antibodies may be produced in a number of ways.

1. The aberrant form of the prion protein eg β-form or aggregated thereof, especially a non-fibrillar aggregate, is purified from the same species as the immunization animal but will usually be human. The aberrant form may alternatively be prepared by purifying (from the animal or from a transferred host cell) the non-aberrant form and converting it to the aberrant form. The immunisation animal may be a "knock-out" mouse, with no prion protein at all. For monoclonal antibodies the animal is normally a mouse; for polyclonal, a rabbit or goat.

2. Raise antibodies to the antigen. For polyclonal antibodies, this is simply a matter of injecting suitably prepared sample into the animal at intervals, and testing its serum for the presence of antibodies (for details, see Dunbar, B. S. & Schwoebel, E. D. (1990) Preparation of polyclonal antibodies. Methods Enzymol. 182, 663–670). But it is essential that the antigen (ie. the protein of interest) be as pure as possible. For monoclonal antibodies, the purity of the antigen is relatively unimportant if the screening procedure to detect suitable clones uses a bioassay.

Antibodies can also be produced by molecular biology techniques, with expression in bacterial or other heterologous host cells (Chiswell, D. J. & McCafferty, J. (1992) Phage antibodies: will new "coli-clonal" antibodies replace monoclonal antibodies?" *Trends Biotechnol.* 10, 80–84). The purification method to be adopted will depend on the source material (serum, cell culture, bacterial expression culture, etc.) and the purpose of the purification (research, diagnostic investigation, commercial production).

The major methods are as follows:

1. Ammonium sulphate precipitation. The γ-globulins precipitate at a lower concentration than most other proteins, and a concentration of 33% saturation is sufficient. Either dissolve in 200 g ammonium sulphate per litre of serum, or add 0.5 vol of saturated ammonium sulphate. Stir for 30 minutes, then collect the γ-globulin fraction by centrifugation, redissolve in an appropriate buffer, and remove excess ammonium sulphate by dialysis or gel filtration.

2. Polyethylene glycol precipitation. The low solubility of γ-globulins can also be exploited using PEG. Add 0.1 vol of a 50% solution of PEG 6,000 to the serum, stir for 30 minutes and collect the y-globulins by centrifugation. Redissolve the precipitate in an appropriate buffer, and remove excess PEG by gel filtration on a column that fractionates in a range with a minimum around 6,000 Da.

3. Isoelectric precipitation. This is particularly suited for IgM molecules, and the precise conditions will depend on the exact properties of the antibody being produced.

4. Ion-exchange chromatography. Whereas most serum proteins have low isoelectric points, γ-globulins are isoelectric around neutrality, depending on the exact properties of the antibody being produced. Adsorption to cation exchangers in a buffer of around pH 6 has been used successfully, with elution with a salt gradient, or even standard saline solution to allow immediate therapeutic use.

5. Hydrophobic chromatography. The low solubility of γ-globulins reflects their relatively hydrophobic character. In the presence of sodium or ammonium sulphate, they bind to many hydrophobic adsorbents, such as "T-gel" which consists of β-mercaptoethanol coupled to divinyl sulphone-activated agarose.

6. Affinity adsorbents. Staphylococcus aureus Outer coat protein, known as Protein A, is isolated from the bacterial cells, and it interacts very specifically and strongly with the invariant region ($F_c$) of immunoglobulins (Kessler, S. W. (1975) Rapid isolation of antigens from cells with a staphylococcal protein A-antibody absorbent: Parameters of the interaction of antibody-antigen complexes with protein A. *J Immunol*. 115, 1617–1624. Protein A has been cloned, and is available in many different forms, but the most useful is as an affinity column: Protein A coupled to agarose. A mixture containing immunoglobulins is passed through the column, and only the immunoglobulins adsorb. Elution is carried out by lowering the pH; different types of IgG elute at different pHs, and so some trials will be needed each time. The differences in the immunoglobulins in this case are not due so much to the antibody specificity, but due to different types of $F_c$ region. Each animal species produces several forms of heavy chain varying in the $F_c$ region; for instance, mouse immunoglobulins include subclasses $IgG_1$, $IgG_{2a}$, and $IgG_3$ all of which behave differently on elution from Protein A. Some γ-globulins do not bind well to Protein A. An alternative, Protein G from G from a Streptococcus sp., can be used. This is more satisfactory with immunoglobulins from farm animals such as sheep, goats and cattle, as well as with certain subclasses of mouse and rabbit IgGs.

The most specific affinity adsorbent is the antigen itself. The process of purifying an antibody on an antigen adsorbent is essentially the same as purifying the antigen on an antibody adsorbent. The antigen is coupled to the activated matrix, and the antibody-containing sample applied. Elution requires a process for weakening the antibody-antigen complex. This is particularly useful for purifying a specific antibody from a polyclonal mixture.

Monoclonal antibodies (MAbs) can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982). {PRIVATE}

Chimaeric antibodies are discussed by Neuberger et al (1988, 8th *International Biotechnology Symposium* Part 2, 792–799).

Suitably prepared non-human antibodies can be "humanized" in known ways, for example by inserting the CDR regions of mouse antibodies into the framework of human antibodies. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parental antibody (Morrison et al (1984) *Proc. Natl. Acad. Sci. USA* 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

A CDR-grafted antibody may be produced having at least one chain wherein the framework regions are predominantly derived from a first antibody (acceptor) and at least one CDR is derived from a second antibody (donor), the CDR-grafted antibody being capable of binding to the β-form PrP antigen. {PRIVATE}

The CDR-grafted chain may have two or all three CDRs derived from the donor antibody.

Advantageously, in the CDR-grafted chain, the or each CDR comprises a composite CDR comprising all the residues from the CDR and all the residues in the corresponding hypervariable region of the donor antibody.

Preferably, at least one residue in the framework regions of the CDR-grafted chain has been altered so that it corresponds to the equivalent residue in the antibody, and the framework regions of the CDR-grafted chain are derived from a human antibody.

Advantageously, the framework regions of the CDR-grafted chain are derived from a human Ig heavy chain. For such heavy chains, it is preferred that residue 35 in the heavy chain framework regions be altered so that it corresponds to the equivalent residue in the donor antibody.

Suitably, for such heavy chains, at least one composite CDR comprising residues 26 to 35, 50 to 65 or 95 to 102 respectively is grafted onto the human framework. It will be appreciated in this case that residue 35 will already correspond to the equivalent residue in the donor antibody.

Preferably, residues 23, 24 and 49 in such heavy chains correspond to the equivalent residues in the antibody. It is more preferred that residues 6, 23, 24, 48 and 49 in such heavy chains correspond to the donor antibody in equivalent residue positions. If desired, residues 71, 73 and 79 can also so correspond.

To further optimise affinity, any one or any combination of residues 57, 58, 60, 88 and 91 may correspond to the equivalent residue in the donor antibody.

The heavy chain may be derived from the human KOL heavy chain. However, it may also be derived from the human NEWM or EU heavy chain.

Alternatively, the framework regions of the CDR-grafted chain may be derived from a human kappa or lambda light chain. For such a light chain, advantageously at least one composite CDR comprising residues 24 to 34, 50 to 56 or 89 to 97 respectively is grafted onto the human framework. Preferably, residue 49 also corresponds to the equivalent residue in the donor antibody.

To further optimise affinity, it is preferable to ensure that residues 49 and 89 correspond to the equivalent residues in the donor antibody. It may also be desirable to select equivalent donor residues that form salt bridges.

The light chain is preferably derived from the human REI light chain. However, it may also be derived from the human EU light chain.

Preferably, the CDR-grafted antibody comprises a light chain and a heavy chain, one or, preferably, both of which have been CDR-grafted in accordance with the principles set out above for the individual light and heavy chains.

It is advantageous that all three CDRs on the heavy chain are altered and that minimal alteration is made to the light chain. It may be possible to alter none, one or two of the light chain CDRs and still retain binding affinity at a reasonable level.

It will be appreciated that in some cases, for both heavy and light chains, the donor and acceptor residues may be identical at a particular position and thus no change of acceptor framework residue will be required.

It will also be appreciated that in order to retain as far as possible the human nature of the CDR-grafted antibody, as few residue changes as possible should be made. It is envisaged that in many cases, it will not be necessary to change more than the CDRs and a small number of framework residues. Only in exceptional cases will it be necessary to change a larger number of framework residues.

Preferably, the CDR-grafted antibody is a complete Ig, for example of isotype $IgG_1$, or $IgG_2$, $IgG_3$ or IgM.

If desired, one or more residues in the constant domains of the Ig may be altered in order to alter the effector functions of the constant domains.

Preferably, the CDR-grafted antibody has an affinity for the β-form PrP antigen of between about $10^5.M^{-1}$ to about $10^{12}.M^{-1}$, more preferably at least $10^8.M^{-1}$.

Advantageously, the or each CDR is derived from a mammalian antibody and preferably is derived from a murine MAb.

Suitably, the CDR-grafted antibody is produced by use of recombinant DNA technology.

A further method for producing a CDR-grafted antibody comprises providing a first DNA sequence, encoding a first antibody chain in which the framework regions are predominantly derived from a first antibody (acceptor) and at least one CDR is derived from a second antibody (acceptor), under the control of suitable upstream and downstream elements; transforming a host cell with the first DNA sequence; and culturing the transformed host cell so that a CDR-grafted antibody is produced.

Preferably, the method further comprises: providing a second DNA sequence, encoding a second antibody chain complementary to the first chain, under the control of suitable upstream and downstream elements; and transforming the host cell with both the first and second DNA sequences.

Advantageously, the second DNA sequence encodes a second antibody chain in which the framework regions are predominantly derived from a first antibody (acceptor) and at least one CDR is derived from the second antibody (donor).

The first and second DNA sequences may be present on the same vector. In this case, the sequences may be under the control of the same or different upstream and/or downstream elements.

Alternatively, the first and second DNA sequences may be present on different vectors.

A nucleotide sequence may be formed which encodes an antibody chain in which the framework regions are predominantly derived from a first antibody (acceptor) and at least one CDR is derived from a second antibody (donor), the antibody chain being capable of forming a CDR-grafted antibody.

The CDR-grafted antibodies may be produced by a variety of techniques, with expression in transfected cells, such as yeast, insect, CHO or myeloma cells, being preferred. Most preferably, the host cell is a CHO host cell.

To design a CDR-grafted antibody, it is first necessary to ascertain the variable domain sequence of an antibody having the desired binding properties. Suitable source cells for such DNA sequences include avian, mammalian or other vertebrate sources such as chickens, mice, rats and rabbits, and preferably mice. The variable domain sequences ($V_H$ and $V_L$) may be determined from heavy and light chain cDNA, synthesized from the respective mRNA by techniques generally known to the art. The hypervariable regions may then be determined using the Kabat method (Wu and Kabat, J. (1970) *J. Exp. Med.* 132, 211). The CDRs may be determined by structural analysis using X-ray crystallography or molecular modelling techniques. A composite CDR may then be defined as containing all the residues in one CDR and all the residues in the corresponding hypervariable region. These composite CDRs along with certain select residues from the framework region are preferably transferred as the "antigen binding sites", while the remainder of the antibody, such as the heavy and light chain constant domains and remaining framework regions, may be based on human antibodies of different classes. Constant domains may be selected to have desired effector functions appropriate to the intended use of the antibody so constructed. For example, human IgG isotypes, $IgG_1$ and $IgG_3$ are effective for complement fixation and cell mediated lysis. For other purposes other isotypes, such as $IgG_2$ and $IgG_4$, or other classes, such as IgM and IgE, may be more suitable.

For human therapy, it is particularly desirable to use human isotypes, to minimise antiglobulin responses during therapy. Human constant domain DNA sequences, preferably in conjunction with their variable domain framework bases can be prepared in accordance with well-known procedures. An example of this is CAMPATH 1H available from Glaxo Wellcome.

Certain CDR-grafted antibodies are provided which contain select alterations to the human-like framework region (in other words, outside of the CDRs of the variable domains), resulting in a CDR-grafted antibody with satisfactory binding affinity. Such binding affinity is preferably from about $10^5.M^{-1}$ to about $10^{12}.M^{-1}$ and is more preferably at least about $10^8.M^{-1}$.

In constructing the CDR-grafted antibodies, the $V_H$ and/or $V_L$ gene segments may be altered by mutagenesis. One skilled in the art will also understand that various other nucleotides coding for amino acid residues or sequences contained in the Fc portion or other areas of the antibody may be altered in like manner (see, for example, PCT/US89/00297).

Exemplary techniques include the addition, deletion or nonconservative substitution of a limited number of various nucleotides or the conservative substitution of many nucleotides, provided that the proper reading frame is maintained.

Substitutions, deletions, insertions or any subcombination may be used to arrive at a final construct. Since there are 64 possible codon sequences but only twenty known amino acids, the genetic code is degenerate in the sense that different codons may yield the same amino acid. Thus there is at least one codon for each amino acid, ie each codon yields a single amino acid and no other. It will be apparent that during translation, the proper reading frame must be maintained in order to obtain the proper amino acid sequence in the polypeptide ultimately produced.

Techniques for additions, deletions or substitutions at predetermined amino acid sites having a known sequence are well known. Exemplary techniques include oligonucleotide-mediated site-directed mutagenesis and the polymerase chain reaction.

Oligonucleotide site-directed mutagenesis in essence involves hybridizing an oligonucleotide coding for a desired mutation with a single strand of DNA containing the region to be mutated and using the single strand as a template for extension of the oligonucleotide to produce a strand containing the mutation. This technique, in various forms, is described in Zoller and Smith (1982) *Nucl. Acids Res.* 10, 6487.

Polymerase chain reaction (PCR) in essence involves exponentially amplifying DNA in vitro using sequence specific oligonucleotides. The oligonucleotides can incorporate sequence alterations if desired. The polymerase chain reaction technique is described in Mullis and Fuloona (1987) *Meth. Enz.* 155, 335. Examples of mutagenesis using PCR are described in Ho et al (1989) *Gene* 77, 51.

The nucleotide sequences, capable of ultimately expressing the desired CDR-grafted antibodies, can be formed from a variety of different polynucleotides (genomic DNA, cDNA, RNA or synthetic oligonucleotides). At present, it is preferred that the polynucleotide sequence comprises a fusion of cDNA and genomic DNA. The polynucleotide sequence may encode various Ig components (eg V, J, D, and C domains). They may be constructed by a variety of different techniques. Joining appropriate genomic and cDNA sequences is presently the most common method of production, but cDNA sequences may also be utilized (see EP-A-0 239 400).

9. Raising an Antibody Response in a Patient

Active immunisation of the patient is preferred. In this approach, one or more β-form PrP proteins or an aggregate thereof, especially a non-fibrillar aggregate, are prepared in an immunogenic formulation containing suitable adjuvants and carriers and administered to the patient. Suitable adjuvants include Freund's complete or incomplete adjuvant, muramyl dipeptide, the "Iscoms" of EP 109 942, EP 180 564 and EP 231 039, aluminium hydroxide, saponin, DEAE-dextran, neutral oils (such as miglyol), vegetable oils (such as arachis oil), liposomes, Pluronic polyols or the Ribi adjuvant system (see, for example GB-A-2 189 141). "Pluronic" is a Registered Trade Mark.

It may be advantageous to use a β-form PrP protein or an aggregate thereof from a species other than the one being treated, in order to provide for a greater immunogenic effect, although on the other hand maturing the species may reduce the likelihood of creating anti-αPrP antibodies. Another compound can be used instead of the whole β-form PrP protein in order to produce inhibitory antibodies in the patient. Such other compounds may include fragments and analogues of the β-form PrP protein.

Skilled persons will appreciate that purification of the β-form and/or β-form binding agents, especially antibodies, can be accomplished by conventional techniques such as affinity chromatography or phage display. By "β-form binding agent" we include any agent which is able to binds preferentially the β-form rather than the α-form of a prion protein. Purification of β-form aggregate binding agents, especially non-fibrillar aggregate binding agents, can also be accomplished by conventional techniques.

The binding agent is preferably an antibody or antigen binding fragment thereof such a Fab, Fv, ScFv and Ab, but it may also be any other ligand which exhibits the preferential binding characteristic mentioned above.

Affinity chromatography is described in Scopes, R. K. (1993) *Protein Purification: principles and practice* 3rd Ed. Springer-Verlag, New York, ISBN 0-387-44072-3, 3-540-94072-3. (See chapters 7 and 9 in particular).

Further information on the above affinity chromatography techniques and the immunoassay of antigen and antibody is provided by Roitt (1991) *Essential Immunology* 7th Ed. Blackwell Scientific Publications, London, ISBN 0-632-02877-7 (see chapter 5 in particular).

The disclosure of the above references is incorporated herein by reference. Nevertheless, an the outline of known methods is described herein.

Purification of Antigens and Antibodies by Affinity Chromatography

Antigen or antibody is bound through its free amino groups to cyanogen-bromide-activated Sepharose particles. Insolubilized antibody, for example, can be used to pull the corresponding antigen out of solution in which it is present as one component of a complex mixture, by absorption to its surface. The unwanted material is washed away and the required ligand released from the affinity absorbent by disruption of the antigen-antibody bonds by changing the pH or adding chaotropic ions such as thiocyanate. Likewise, an antigen immunosorbent can be used to absorb out an antibody from a mixture whence it can be purified by elution. The potentially damaging effect of the eluting agent can be avoided by running the anti-serum down an affinity column so prepared as to have relatively-weak binding for the antibody being purified; under these circumstances, the antibody is retarded in flow rate rather than being firmly bound. If a protein mixture is separated by iso-electric focusing into discrete bands, an individual band can be used to affinity purify specific antibodies from a polyclonal antiserum.

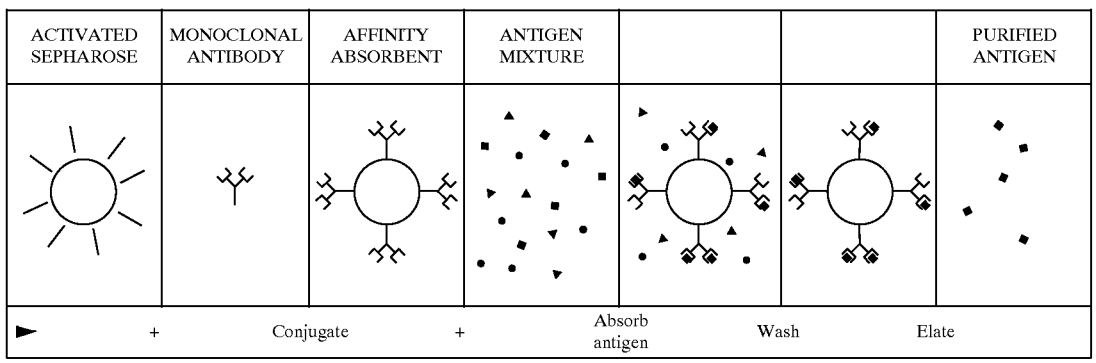

Affinity chromatography. A column is filled with Sepharose-linked antibody. The antigen mixture is poured down the column. Only the antigen binds and is released by change in pH for example. An antigen-linked affinity column will purify antibody obviously.

Immunoassay of Antigen and Antibody with Labelled Reagents

Antigen and antibody can be used for the detection of each other and a variety of immunoassay techniques have been developed in which the final read-out of the reaction involves a reagent conjugated with an appropriate label. Radiolabelling with $^{131}$I, $^{125}$I, is an established technique.

Soluble Phase Immunoassays

Radioimmunoassay (RIA) for Antigen serum is added to a microwell coated with antigen, the antibodies will bind to the plastic and remaining serum proteins can be readily washed away. Bound antibody can be estimated by addition of $^{125}$I-labelled purified rabbit anti IgG; after rinsing out excess unbound reagent, the radioactivity of the rube will be a measure of the antibody content of the patient's serum. The distribution of antibody in different classes can obviously be determined by using specific antisera.

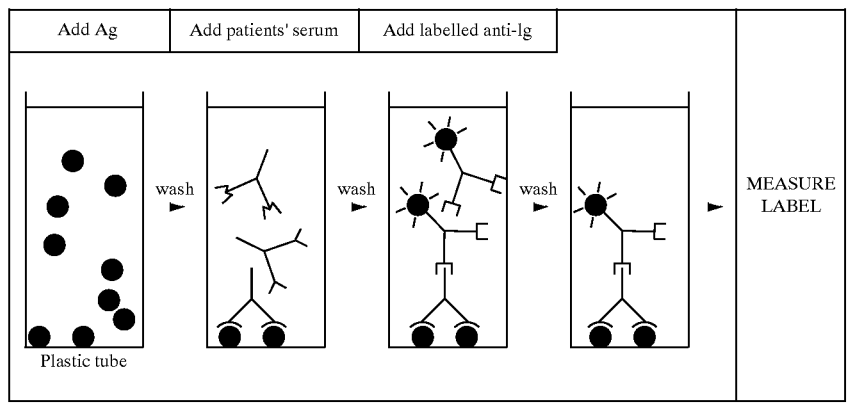

Solid phase immunoassay for antibody. By attaching antibody to the solid phase, the system can be used to assign antigen. To reduce non-specific binding of IgG to the solid phase after absorption of the first reagent, it is usual to add an irrelevant protein such as gelatin, or more recently $\alpha_1$- glycoprotein, to block any free sites on the plastic.

The binding of radioactively labelled antigen to a limited fixed amount of antibody can be partially inhibited by addition of unlabelled antigen and the extent of this inhibition can be used as a measure of the unlabelled material added.

For Antibody

The antibody content of a serum can be assessed by the ability to bind to antigen which has been in and immobilised by physical absorption to a plastic tube or microagglutination tray with multiple wells; the bound immunoglobin may then be estimated by addition of a labelled anti-Ig raised for anther species. For example, a patient's Immunoradiometric Assay for Antigen This differs from radioimmunoassay in the sense that the labelled reagent is used in excess. For the estimation of antigen, antibodies are coated on to a solid surface such as plastic and the test antigen solution added; after washing, the amount of antigen bound to the plastic can be estimated by adding an excess of radio-labelled antibody. The specificity of the method can be improved by the sandwich assay which uses solid phase and labelled antibodies with specificities for different parts of the antigen:

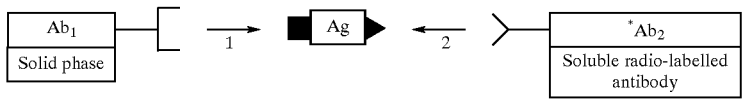

Because of health hazards and the deterioration of reagents through radiation damage, types of label other than radiosotopes have been sought.

ELISA (Enzyme-linked Immunosorbent Assay)

Perhaps the most widespread alternative has been the use of enzymes which give a coloured reaction product, usually in solid phase assays. Enzymes such as horse radish peroxidase and phosphatase have been widely employed. A way of amplifying the phosphatase reaction is to use NADP as a substrate to generate AND which now acts as a coenzyme for a second enzyme system. Pyrophosphatase from $E.coli$ provides a good conjugate because the enzyume is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

10. Identification of Ligands by Phage Display

The display of proteins and polypeptides on the surface of bacteriophage (phage), fused to one of the phage coat proteins, provides a powerful tool for the selection of specific ligands. This 'phage display' technique was originally used by Smith in 1985 (*Science* 228, 1315–7) to create large libraries of antibodies for the purpose of selecting those with high affinity for a particular antigen. More recently, the method has been employed to present peptides, domains of proteins and intact proteins at the surface of phages in order to identify ligands having desired properties.

The principles behind phage display technology are as follows:

(i) Nucleic acid encoding the protein or polypeptide for display is cloned into a phage;

(ii) The cloned nucleic acid is expressed fused to the coat-anchoring part of one of the phage coat proteins (typically the p3 or p8 coat proteins in the case of filamentous phage), such that the foreign protein or polypeptide is displayed on the surface of the phage;

(iii) The phage displaying the protein or polypeptide with the desired properties is then selected (e.g. by affinity chromatography) thereby providing a genotype (linked to a phenotype) that can be sequenced, multiplied and transferred to other expression systems.

Alternatively, the foreign protein or polypeptide may be expressed using a phagemid vector (i.e. a vector comprising origins of replication derived from a phage and a plasmid) that can be packaged as a single stranded nucleic acid in a bacteriophage coat. When phagemid vectors are employed, a "helper phage" is used to supply the functions of replication and packaging of the phagemid nucleic acid. The resulting phage will express both the wild type coat protein (encoded by the helper phage) and the modified coat protein (encoded by the phagemid), whereas only the modified coat protein is expressed when a phage vector is used.

Methods of selecting phage expressing a protein or peptide with a desired specificity are known in the art. For example, a widely used method is "panning", in which phage stocks displaying ligands are exposed to solid phase coupled target molecules, e.g. using affinity chromatography.

Alternative methods of selecting phage of interest include SAP (Selection and Amplification of Phages; as described in WO 95/16027) and SIP (Selectively-Infective Phage; EP 614989A, WO 99/07842), which employ selection based on the amplification of phages in which the displayed ligand specifically binds to a ligand binder. In one embodiment of the SAP method, this is achieved by using non-infectious phage and connecting the ligand binder of interest to the N-terminal part of p3. Thus, if the ligand binder specifically binds to the displayed ligand, the otherwise non-infective ligand-expressing phage is provided with the parts of p3 needed for infection. Since this interaction is reversible, selection can then be based on kinetic parameters (see Duenas et al., 1996, *Mol. Immunol.* 33, 279–285).

The use of phage display to isolate ligands that bind biologically relevant molecules has been reviewed in Felici et al. (1995) *Biotechnol. Annual Rev.* 1, 149–183, Katz (1997) *Annual Rev. Biophys. Biomol. Struct.* 26, 27–45 and Hoogenboom et al. (1998) *Immunotechnology* 4(1), 1–20. Several randomised combinatorial peptide libraries have been constructed to select for polypeptides that bind different targets, e.g. cell surface receptors or DNA (reviewed by Kay, 1995, *Perspect. Drug Discovery Des.* 2, 251–268; Kay and Paul, 1996, *Mol. Divers.* 1, 139–140). Proteins and multimeric proteins have been successfully phage-displayed as functional molecules (see EP 0349578A, EP 0527839A, EP 0589877A; Chiswell and McCafferty, 1992, *Trends Biotechnol.* 10, 80–84). In addition, functional antibody fragments (e.g. Fab, single chain Fv [scFv]) have been expressed (McCafferty et al., 1990, *Nature* 348, 552–554; Barbas et al., 1991, *Proc. Natl. Acad. Sci. USA* 88, 7978–7982; Clackson et al., 1991, *Nature* 352, 624–628), and some of the shortcomings of human monoclonal antibody technology have been superseded since human high affinity antibody fragments have been isolated (Marks et al., 1991, *J. Mol. Biol.* 222, 581–597; Hoogenboom and Winter, 1992, *J. Mol. Biol.* 227, 381–388). Further information on the principles and practice of phage display is provided in *Phage display of peptides and proteins: a laboratory manual Ed Kay*, Winter and McCafferty (1996) Academic Press, Inc ISBN 0-12-402380-0, the disclosure of which is incorporated herein by reference.

11. Immunisation—Preferred Protocols

11a. Preparation of Antigen

For the preparation of monoclonal antibodies (mAbs), β-PrP or its derivatives may be provided in an acetate buffer as described above. Antigens may be physically (by creating recombinant β-PrP fusion proteins) or chemically coupled to suitable carrier proteins to provide additional T cell help for immunisation in $PRNP^{+/+}$ mice and other rodents.

11b. Mice of various strains, rats, hamsters or rabbits can be inoculated subcutaneously with β-PrP (or an aggregate thereof, especially a non-fibrillar aggregate (50–100 μg/animal), emulsified in complete/incomplete Freunds adjuvant at 3 weekly intervals (Days 0,20,41). At day 37 anti-peptide activity can be assayed by ELISA. On day 48 in the case of animals used for mAb production, a final intraperitoneal boost can be given and the animals killed for fusion 3 days later (day 50). In the case of rabbits inoculated to produce polyclonal antibodies, the animals may be bled after the final boost, and at regular subsequent intervals with or without further inoculation depending on anti-β PrP titre.

12. Monoclonal Antibody Preparation

Routine methods may be used (Galfre G., and Milstein, C. 1981 *Methods in Enzymology* 73, 3–46)

12a. Myeloma Cells

The following fusion partners may be used:

| Mouse | NSO/u | Clark M. R., and Milstein, C. 1982 Somatic Cells Genetics 7, 657–666 |
| --- | --- | --- |
| | X63/Ag 8.653 | Keraney et al. 1979 J. Immunol. 123, 1548–1550 |
| | SP2/0 | Sanchez-Madrid et al 1983 J. Immunol 130, 309–312 Bluestone 1987 PNAS 84, 1374 |
| Rat fusions | Y3 (210.RCY3.Ag 1.2.3)YO | Galfre G., and Milstein, C. 1981 Methods in Enzymology 73, 3–46 |
| Hamster fusions | SP2/0 | |

11b. Fusion Procedure

Two spleens from mice that have produced high titre antibody are fused. Myeloma cells growing in exponential phase may be mixed with splenic single cell suspensions in appropriate ratios, washed free of serum, and then gently resuspended in a 50% polyethylene glycol solution at 37° C. followed after 1–2 minutes with increasing volumes of serum-free medium. After a further incubation in RPMI/ 10% foetal calf serum ($RF_{10}$) at 37° C. week and thereafter in RF10. At day 10–14 positive wells are screened for anti-PrP antibody by ELISA. Positive wells are then repeatedly cloned by limiting dilution until stable. Hybridomas cryopreserved in FCS 10% DMSO are stored in liquid $N_2$ dewars.

13. Screening for Anti-β PrP Antibodies in Serum

Recombinant PrP (0.5–10 μg/well), may be dialysed against appropriate coating buffer (pH 4–10) and adsorbed to standard ELISA plates for 30–60 minutes at 37° C. prior to washing x4 in PBS/Tween 0.05% (PBST). After blocking in PBS/BSA 2% with or without additional sera, dilutions of serum are incubated in duplicate as are relevant negative and positive controls. After washing, the peroxidase conjugated anti-IgG secondary is incubated, washed and then fresh ortho-phenyl diamine (OPD) substrate added. Finally after stopping the reaction with 3M sulphuric acid the absorbance is measured at 492 nm.

14. Screening Culture Supernatants for $PrP^{Sc}$-specific Monoclonal Antibodies This may involve a staged two day procedure. On day 1, 50 μl of the growing cultures may be screened for anti-β PrP IgG as in the ELISA described above. This β-PrP may or may not be first digested with proteinase K to remove any alpha PrP species. Positive wells in this assay may then be screened the following day in a dot blot assay modified from Collinge et al 1995 *Lancet* 346:569–570. Dot blot apparatus (ELIFA, Pierce Wariner) can be used that allows the simultaneous screening of multiple supernatants. Supernatants can be screened for binding to recombinant β-PrP, 1% normal human brain homogenate and to a pool of 1% homogenates from CJD brains containing types 1–4, thus enabling the preferential selection of $PrP^{Sc}$-specific mAbs. Thus only mAbs that bind infectious prions and not $PrP^{c}$ from normal brain will be expanded. Alternatively, culture supernantants can be screened for preferential binding to either alpha or β-PrP, or to synthetic peptides to which $PrP^{Sc}$-specific mAbs may bind. The 15B3 $PrP^{Sc}$-specific mAb cross-reacts with human, bovine and murine $PrP^{Sc}$, and its epitope has been mapped with linear synthetic peptides to three regions on the bovine PrP molecule: residues 142–148, 162–170 and 214–226 and later two of which may not be recognised by antibodies that bind to both $PrP^{c}$ and $PrP^{Sc}$ (Korth C. et al. 1997 *Nature* 390, 74–77). These peptides are adsorbed to ELISA plates with poly-lysine.

Monoclonal Antibodies Raised Against β-PrP

β-PrP is highly immunogenic in Prn-$p^{0/0}$ (PrP null) mice immunised subcutaneously with soluble or aggregated protein emulsified in Freund's adjuvant and splenocytes from hyperimmunised PrP null mice can be readily fused with various fusion partners (eg NSO, NS1 murine myeloma cells). One of the major advances of using β-PrP when making monoclonal antibodies is its use in screening. Previously, high throughput hybridoma screening has not been possible given the small amounts of available purifiable native PrP. We have now developed a rapid $PrP^{c}/PrP^{sc}$ discriminating ELISA screening protocol using recombinant PrP folded into either alpha or beta conformations. To date we have found that some mAbs recognise only alpha PrP and others recognise both alpha and beta conformations. We presume that $PrP^{sc}$-specific mAbs will recognise recombinant beta PrP and not alpha recombinant protein. An early rejection of alpha-only binding mAbs dramatically increases the efficiency of the screening process. Additional information regarding mAb epitopes has been obtained using responses to recombinant alpha and beta PrP pre-digested or not with varying concentrations of proteinase K.

We have now produced 32 monoclonal anti-PrP antibodies using standard hybridoma technology. The majority of these mAbs recognise native alpha PrP in dot blots and on the surface of a wide variety of cells in flow cytometric analyses as well as denatured PrP derived from normal or TSE brain homogenates.

15. Characterisation of mAbs

Immunoglobin subclass and culture supernatant Ig concentration can be measured by standard ELISA techniques. The fine specificity of $PrP^{c}$ or $PrP^{Sc}$ specific mAbs can be defined either by using a gridded array of overlapping human PrP peptides (synthesised commercially by Jerino Bio Tools GMbH) or by using pools of PrP synthetic peptides (synthesised individually using standard f-moc chemistry) in the standard ELISA. Measurements of the affinity of anti-PrP mAbs for their ligands can be lo made using surface plasmon resonance. Direct comparisons can be made of mAb binding to alpha and β-PrP molecules.

16. Binding of mAbs to Surface Bound and Intracellular PrP

Flow cytometry and immunofluorescence microscopy may be used to study surface and intracellular $PrP^{c}/PrP^{Sc}$ expression in cell lines that express surface PrP (eg EVBV lymphoblastoid, U937, K562, HEl) and peripheral blood mononuclear cells.

17. Binding to PrP in Tissue Sections

Both acetone fixed fresh frozen sections and fixed paraffin embedded sections from normal and CJD/BSE/scrapie tissue can be used to assess the usefulness of β-PrP binding mAbs in routine immunohistochemistry.

18. Use of Antibody in the Diagnosis of a Prion Disease

The detection of the disease-associated isoform of prion protein, PrP$^{Sc}$, in brain or other tissues from patients is thought to be diagnostic of prion disease. To distinguish PrP$^{Sc}$ from its cellular precursor, PrP$^c$, requires either pretreatment with proteinase K, which will completely digest PrP$^c$, but only removes a protease-sensitive N-terminal of PrP$^{Sc}$ or, alternatively, would require an antibody which distinguished between PrP$^c$ and PrP$^{Sc}$. Only one such selective antibody (Korth C. et al. 1997 Nature 390, 74–77) has yet been reported and appears to be able to selectively immunoprecipitate PrP$^{Sc}$. It is not clear as yet, however, whether this antibody offers any increase in diagnostic sensitivity over existing monoclonals. It is an IgM antibody and is likely to be of low affinity for PrP$^{Sc}$. By using recombinant human PrP, and in particular the β-form of the invention, or an aggregate thereof, especially a non-fibrillar aggregate, we should produce antibodies with high diagnostic sensitivity as well as specificity. Anti β-PrP antibodies may be PrP$^{Sc}$-specific or, alternatively, detect low levels of β-PrP monomer in blood or other tissues or bodily fluids or materials, including faeces, urine, sputum, lymph, lymph nodes, tonsil, appendix tissue, cerebrospinal fluid, or derivatives or components thereof.

Skilled persons will appreciate that the β-form specific binding agents such as antibodies of the invention can be used in subtraction assays which involve pretreatment of a sample with a binding agent such as an antibody specific for the normal cellular α-form of a prion protein, Prp$^C$, followed by treatment with a β-form specific binding agent eg antibody and detection of anti β-form binding. The pretreatment step increases the sensitivity of the assay for the β-form.

Similar subtraction methods are described in WO98/16834.

Many detection systems are available for using a monoclonal antibody to diagnose a disease. A number of possibilities are discussed below:

19. Detection of PrP$^{Sc}$ in Body Fluids or Tissue Homogenates a. Sandwich ELISA can be used to detect PrP$^{Sc}$ in body fluids eg serum or cerebropsinal fluid (CSF). This relies on using immobilised ultrasensitive PrP$^{Sc}$-specific mAbs to capture PrP$^{Sc}$ in solution and then using biotinylated mAbs or rabbit polyclonal antiserum with specificity for alternative PrP epitopes to detect the immobilised complexes. The same techniques can be used to detect PrP$^{Sc}$ in tissue homogenates.

b. Dot blots may be used. Here tissue homogenates are placed directly on a suitable membrane and be treated with proteinase K to remove PrP$^c$. The membrane can be incubated with anti-PrP antibodies and then such binding detected using an appropriate, labelled secondary antibody. Various labelling systems, involving enzymatic, fluorescent, radioisotopic or chemiluminescent methods are commonly used.

c. Standard Western blotting techniques can be used. These methods allow not only the detection of PrP, but of specific patterns of banding following proteinase K digestion. These patterns allow the recognition of distinct strains of prions and allow, for instance, the differentiation of new variant CJD from classical CJD (see Collinge et al. 1996 Nature 383, 685–690 and international PCT patent application published as WO 98/16834).

d. Diagnostic methods may be developed based on the differential affinity of anti-PrP mAbs for PrP$^c$ and PrP$^{Sc}$. Surface plasmon resonance is ideally suited for this purpose. In such assays, purified anti-PrP mAbs are immobilised and binding to solubilised PrP measured directly from tissue fluids and homogenates. Enrichment of PrP$^{Sc}$ by differential centrifugation or affinity purification may be required prior to the above assays.

20. Detection of Cell Associated PrP$^{Sc}$

It is likely that the levels of PrP$^{Sc}$ in peripheral blood mononuclear cells (PBMC) of vCJD patients will be low and detection will depend on optimising methods for surface and intracellular detection of PrP and then identifying lymphocyte sub-populations with the highest prion load. Anti-β PrP mAbs can be purified and conjugated to biotin of fluorochromes for this purpose. Dual and three colour flow cytometry can be used to identify the PrP$^{Sc}$ bearing cell types. After surface staining by conventional techniques, intracellular PrP can be detected after fixation and permeabilisation of the cell membranes. Cellular manipulation (eg stimulation of proliferation of the pharmacological blockade of intracellular secretory or endocytic pathways) may be used to enhance PrP detection.

21. Immunohistochemistry

Prion disease may be diagnosed by abnormal patterns of PrP immunoreactivity on either formalin fixed, or frozen, tissue sections using established immonohistochemical detection techniques. Frozen tissue sections of whole brains (histoblots) may be treated with proteinase K and similarly exposed to antibodies to detect patterns of PrP$^{Sc}$ deposition which may also allow discrimination of prion strain types.

22. Detection of Anti-PrP$^{Sc}$ Antibodies in TSE

Although it is assumed that anti-PrP$^{Sc}$ is not induced during the course of natural scrapie infection, this has not been studied sytematicially in any form of CJD. Thus to detect anti-PrP$^{Sc}$ we may absorb β-PrP to immunosorbent plates and perform standard ELISA as above.

23. Detection of PrP Using Highly Sensitive in Vitro Lymphocyte Assays

Specific T cells are extremely sensitive to the presence of their cognate antigen. PrP-specific T cell lines/clones raised in PRNP$^{0/0}$ mice can be used to detect PrP$^{Sc}$ after its absorption to immunomagnetic particles using PrP$^{Sc}$-specific mAbs (after Hawke et al 1992 Journal of Immunological Methods 155(1):41–48). In this method PrP$^{Sc}$ absorbed to the particles is co-cultured with specific T lymphocytes and antigen presenting cells and proliferation (using standard $^3$H-thymidine incorporation assays) and/or cytokine release is measured.

24. Toxicity of β-PrP

To examine the effect of β-PrP, in vivo, mice were inoculated with soluble (low salt) and aggregated (200 mM NaCl) forms of the recombinant murine protein. The recombinant, cellular PrP$^C$ form was also included in the experiment as a control.

By "low salt" we mean an ionic strength which is insufficient to cause aggregation of β-PrP, for example 0 mM to 25 mM.

The salt-treated, aggregated β-PrP material has two forms, as identified by electron microscopy. Addition of 200 mM NaCl causes a rapid formation (<1 hour) of spherical particles (10–20 nm diameter) and further incubation (>24 hours) leads to the formation of fibrillar structures. Because salt addition leads to a time-dependent change in the structure of β-PrP, three different inocula were used: low salt, short salt incubation (2-minutes) and long salt incubation (30 hours).

In order to test whether any pathological effects were dependent on expression of $PrP^C$ in the recipient, two mouse genotypes were used: TG20 (over-expressing mouse PrP) and SV129/B6 (PrP ablated).

Ablated mice are described in Beuler, H., 1992 *Nature* 356:577–582.

TG20 mice are described in Fischer, M., 1996 *The EMBO Journal* 15(6): 1255–1264.

Animals were anaesthetised and inoculated intra-cranially with 30 μL aliquots of protein solution (1.6 mg/ml). After recovery from the anaesthetic some of the mice suffered immediate and severe fits and died within 5 minutes. This acute toxicity was most prevalent in the TG20 mice after inoculation with β-PrP which had undergone a short salt incubation. The PrP-ablated mice showed no susceptibility to β-PrP in any of its 3 forms. The results are given in the table below.

|  | TG20 ($PrP^c$ over expression) | SV129/B6 (PrP ablated) |
| --- | --- | --- |
| $PrP^c$ | 0/8 | N.D. |
| β-PrP - soluble, low salt | 4/10 | 0/10 |
| β-PrP-200 mM NaCl short incubation | 5/10 | 0/10 |
| β-PrP-200 mM NaCl long incubation | 1/10 | 1/10 |
| Buffer control | 0/10 | N.D |

N.D. = none detected.

The toxicity of β-PrP in these circumstances is acute and therefore it can be argued that the effect is unlike that seen in chronic T.S.E.s. However, the amount of PrP material introduced into the brain (~50 μg) is extremely large and, more importantly, the effect is mediated by $PrP^C$. Given that T.S.E.s can only infect animals which express $PrP^C$, it is likely that the effects elicited by β-PrP in this experiment are relevant to prion diseases. One hypothesis which is consistent with the above observations is that the toxic agent in T.S.E.s is not the fibrillar insoluble material but a transiently formed low molecular weight form which goes on to form these high-order aggregates. This toxic material never reaches high steady-state levels during the disease and so the rate of synaptic loss and cell death is slow. When large quantities are introduced in a single dose then there is a sudden, widespread effect on neurones which, in this initial phase, leads to sustained depolarisation and the consequent fits. The fact that this effect is only seen on neurones with endogenous $PrP^C$ suggests that the effect is mediated by interactions between β-PrP and $PrP^C$. In the chronic Prion diseases there is only sufficient β-PrP at any one time to affect a small number of neurones, but long-term exposure to low levels of the agent leads to a slow loss of synaptic connections and eventual death of cells. We term this lethal form of the protein $β-PrP^L$.

This represents the first occasion on which toxic Prions have been made in vitro and the results demonstrate the importance of our production and characterisation of the soluble β-form precursor of the toxic aggregated material.

25. Identification of Compounds Capable of Inhibiting and/or Reversing Conversion of a Prion Protein from its α Conformation to a β-Conformation or from β-form to Aggregated and/or Amyloid Form, Especially a Non-fibrillar Aggregate.

Use of β-PrP in High-throughput Screening for Potential Therapeutics

The experiments thus far performed on the β-PrP structure can be summarised:

α-PrP(reduced, monomeric) ⇌ β-PrP(reduced, monomeric)
↓
PrP aggregated and/or amyloid The first transition is reversible, with the β-PrP conformation being favoured by lowering the pH to an acidic pH, for example pH 4. The second transition is effectively irreversible and results in the formation of the aggregated and/or amyloid, especially a non-fibrillar aggregate, form which scatters light owing to the large particle size. The system can be kept in the monomeric β-PrP form by maintaining a low ionic strength eg 20 mM NaCl or equivalent. When the ionic strength is raised (by use of guanidinium chloride, sodium chloride, or potassium chloride at a concentration of from 100–200 mM, especially 200 mM or more, for instance) the system shifts towards the aggregated and/or amyloid state.

The availability and understanding of this system allows the design of routine and rapid assays for compounds which prevent aggregated and/or amyloid formation, especially the toxic non-fibrillar aggregate mentioned in section 24.

The simplest and technically most direct method is to screen for any compound which blocks the second transition by poising the system in the β-PrP (reduced, monomeric) state at pH 4 and low ionic strength, for example 200 mM NaCl. Compounds will then be added to this protein solution and incubated in screening wells. The next step will be to increase the ionic strength by the addition of NaCl, KCl or similar compound which would normally promote the formation of the aggregated and/or amyloid form and cause an increase in light scattering in the 400–500 nm range of wavelengths. Any compound, added at the first stage, which was capable of binding to and stabilising either the α-PrP (reduced, monomeric) form and/or the β-PrP (reduced, monomeric) form will show a low scattering signal in the relevant well.

Such a system can be rapidly optimised for a high throughput screen by use of large, multi-well microtitre plates handled by robotic systems. Screening of hundreds of thousands of different compounds is then entirely feasible over a timescale of several months. Even larger scale screens, of millions of compounds, is also entirely possible with allocation of sufficient technical resources. Assuming sufficient diversity within the chemical libraries screened, it ought to be possible to identify compounds which inhibit β-PrP or aggregated β-PrP formation at extremely low concentration, which can then be further evaluated.

Recombinant β-PrP: Vaccine Potential

Disruption of the transformation of normal cellular PrP is potentially achievable using antibodies directed at either $PrP^c$ of $PrP^{sc}$ or both. However, it has long been recognised that anti-PrP immunity is not induced during the course of natural TSE. This can be most readily explained by the widespread expression of tolerogenic levels of PrP in the lymphoreticular system; particularly in the thymus where T cells develop. Unless helper T cells are stimulated by an immunogen, B cells will not be driven to differentiate into antibody-secreting plasma cells. It is known that physical linkage of a 'carrier' protein to the antibody target may overcome the need for its recognition by T cells. Despite the fact that $PrP^c$ is expressed on many haemopoetic cells in the bone marrow making tolerance of PrP-binding B cells also likely, we have been able to conjugate carrier proteins to both recombinant alpha and beta PrP and induce anti-PrP antibodies in wild-type mice; even using mouse recombinant protein conjugates as immunogens. We have also found that T cell help can be provided by immunising mice with human recombinant PrP in either alpha or beta conformations. Presumably the sequence differences between mouse and human PrP are the stimulating T cell epitopes. Both of these approaches are currently being tested for disease modifying potential and they may form the basis of therapeutic/preventative vaccination for CJD and other TSE.

26. Production of Compounds Comprising a Portion Capable of Binding Preferentially to the β-form of a Prion Protein and a Further Effector Portion In one preferred embodiment the compound comprises an effector portion which is directly or indirectly cytotoxic.

Methods for the preparation of compounds which possess a target-specific binding portion and a directly, or indirectly, cytotoxic portion are well known in the art.

For example, Bagshawe and his co-workers have disclosed (Bagshawe (1987) *Br. J. Cancer* 56, 531; Bagshawe et al. (1988) *Br. J. Cancer* 58, 700; WO 88/07378) conjugated compounds comprising an antibody or part thereof and an enzyme which converts an innocuous pro-drug into a cytotoxic compound. The cytotoxic compounds were alkylating agents, e.g. a benzoic acid mustard released from para-N-bis(2-chloroethyl)aminobenzoyl glutamic acid by the action of Pseudomonas sp. CPG2 enzyme.

An alternative system using different pro-drugs has been disclosed (WO 91/11201) by Epenetos and co-workers. The cytotoxic compounds were cyanogenic monosaccharides or disaccharides, such as the plant compound amygdalin, which releases cyanide upon the action of a β-glucosidase and hydroxynitrile lyase.

In a further alternative system, the use of antibody-enzyme conjugates containing the enzyme alkaline phosphatase in conjunction with the pro-drug etoposide 4'-phosphate or 7-(2'aminoethyl phosphate) mitomycin or a combination thereof have been disclosed (EP 0 302 473; Senter et al., (1988) *Proc. Natl. Acad. Sci. USA* 85, 4842).

Another approach is the in vivo application of streptavidin conjugated antibodies followed, after an appropriate period, by radioactive biotin (Hnatowich et al. (1988) J. Nucl. Med. 29, 1428–1434), or injection of a biotinylated mAb followed by radioactive streptavidin (Paganelli et al. (1990) *Int. J. Cancer* 45, 1184–1189).

Further examples of the targeting of compounds which are directly, or indirectly, cytotoxic are disclosed in PCT/GB94/00087 (EP 0 815 872 A2).

27. Exemplary Pharmaceutical Formulations of the Invention

The formulations may conveniently be presented in unit dosage form and may be prepared by any of the methods well known in the art of pharmacy. Such methods include the step of bringing into association the active ingredient (compound of the invention β-form of a prion protein or an aggregate thereof, or a binding agent, including antibody) with the carrier which constitutes one or more accessory ingredients. In general the formulations are prepared by uniformly and intimately bringing into association the active ingredient with liquid carriers or finely divided solid carriers or both, and then, if necessary, shaping the product.

Whilst it is possible for an agent eg compound of the invention to be administered alone, it is preferable to present it as a pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen free.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The following examples illustrate pharmaceutical formulations according to the invention in which the active ingredient is selected from one or more of antibodies and agents eg compounds of the invention:

EXAMPLE A

Tablet

| | |
|---|---|
| Active ingredient | 100 mg |
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

EXAMPLE B

Ophthalmic Solution

| | |
|---|---|
| Active ingredient | 0.5 g |
| Sodium chloride, analytical grade | 0.9 g |
| Thiomersal | 0.001 g |
| Purified water to | 100 ml |
| pH adjusted to | 7.5 |

EXAMPLE C

Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 500 | 300 |

Formulation B

| | mg/tablet | mg/tablet |
|---|---|---|
| (a) Active ingredient | 250 | 250 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 500 | 300 |

Formulation C

| | |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose used in formulation E is of the direction compression type.

Formulation D

| | mg/capsule |
|---|---|
| Active Ingredient | 250 |
| Pregelatinised Starch NF15 | 150 |
| | 400 |

Formulation E

| | mg/capsule |
|---|---|
| Active Ingredient | 250 |
| Lactose | 150 |
| Avicel ® | 100 |
| | 500 |

Formulation F (Controlled Release Formulation)

The formulation is prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) ® | 112 |
| (c) Lactose B.P. | 53 |

|  | mg/tablet |
| --- | --- |
| (d) Povidone B.P.C. | 28 |
| (e) Magnesium Stearate | 7 |
|  | 700 |

Drug release takes place over a period of about 6–8 hours and is generally complete after 12 hours.

EXAMPLE D

CAPSULE FORMULATIONS

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
| --- | --- |
| (a) Active ingredient | 250 |
| (b) Lactose B.P. | 143 |
| (c) Sodium Starch Glycolate | 25 |
| (d) Magnesium Stearate | 2 |
|  | 420 |

Formulation C

|  | mg/capsule |
| --- | --- |
| (a) Active ingredient | 250 |
| (b) Macrogol 4000 BP | 350 |
|  | 600 |

Capsules are prepared by melting the Macrogol 4000 BP, dispersing the active ingredient in the melt and filling the melt into a two-part hard gelatin capsule.

Formulation D

|  | mg/capsule |
| --- | --- |
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
|  | 513 |

EXAMPLE E

Injectable Formulation

| Active ingredient | 0.200 g |
| --- | --- |
| Sterile, pyrogen free phosphate buffer (pH 7.0) to 10 ml | |

The active ingredient is dissolved in most of the phosphate buffer (35–40° C.), then made up to volume and filtered through a sterile micropore filter into a sterile 10 ml amber glass vial (type 1) and sealed with sterile closures and overseals.

EXAMPLE F

Intramuscular injection

| Active ingredient | 0.20 g |
| --- | --- |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE G

Syrup Suspension

| Active ingredient | 0.2500 g |
| --- | --- |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

EXAMPLE H

Suppository

|  | mg/suppository |
| --- | --- |
| Active ingredient (63 μm)* | 250 |
| Hard Fat, BP (Witepsol H15 - Dynamit Nobel) | 1770 |
|  | 2020 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

EXAMPLE I

Pessaries

|  | mg/pessary |
| --- | --- |
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

28. Use in Medicine

The aforementioned β-form or an aggregate thereof or a binding agent including antibodies and other agents eg compounds of the invention or a formulation thereof may be administered in a variety of ways, for non-limiting example, by any conventional method including oral and parenteral (eg subcutaneous or intramuscular) injection. The treatment may consist of a single dose or a plurality of doses over a period of time, depending on the characteristics of the patient and/or the particular prion disease against which the treatment is directed.

REFERENCES

1. Pan K. M., Baldwin M. A., Nguyen J., et al., *Proc Natl Acad Sci USA*, 90, 10962–10966 (1993).
2. Prusiner S. B., *Science*, 252, 1515–1522 (1991).
3. Riek R., Hornemann S., Wider G., Billeter M., Glockshuber R. and Wuthrich K, *Nature*, 382, 180–182 (1996) {PRIVATE}.
4. James T. L., Liu H., Ulyanov N. B., et al, *Proc Natl Acad Sci USA*, 94, 10086–10091 (1997).
5. Zahn R., Von Schroetter C. and Wüthrich K., *FEBS Lett*, 417, 400–404 (1997).
6. Hornemann S. and Glockshuber R., *J Mol Biol*, 261, 614–619 (1996).
7. Fink A. L., *Fold Des*, 3, R9–23 (1998).
8. Hornemann S. and Glockshuber R., *Proc Natl Acad Sci USA*, 95, 6010–6014 (1998).
9. Ptitsyn O. B. and Uversky V. N., *FEBS Lett*, 341, 15–18 (1994).
10. Ptitsyn O. B., *Adv Protein Chem*, 47, 83–229 (1995).
11. Clark A. R. and Waltho J. P., *Curr Opin Biotechnol*, 8, 400–410 (1997).
12. Chyan C. L., Wornald C., Dobson C. M., Evans P. A. and Baum J., *Biochemistry*, 32, 5681–5691 (1993).
13. Alexandrescu, A. T., Evans, P. A., Pitkeathly, M., Baum, J. & Dobson, C. M. Biochemistry 32, 1707–1718 (1993).
14. Eliezer D., Yao J., Dyson H. J. and Wright P. E., *Nat Struct Biol*, 5, 148–155 (1998).
15. Collinge J., *Hum Mol Genetics*, 6, 1699–1705 (1997).
16. Collinge J., Palmer M. S. and Dryden A. J., *Lancet*, 337, 1441–1442 (1991).
17. Chen Y. H., Yang J. T. and Martinex H. M., *Biochemistry*, 11, 4120–4131 (1972).
18. Ptitsyn O B. [news] *Nat. Struct.Biol* 1996; 3:488–490
19. Ptitsyn O B. *Adv.Protein Chem* 1995; 47: 830229
20. Ptitsyn O B. et al. *Philos.Trans.R.Soc. Land. B. Biol Sci* 1995; 348: 35041
21. Ptitsyn O B. *Curr.Opin.Struct.Biol* 1995; 5: 74–78
22. Ptitsyn O B. *Protein Eng.* 1994; 7: 593–596
23. Ptitsyn O B, Uversky V N. *FEBS Lett*. 1994; 341: 15–18

---

What is claimed is:

1. A purified monomeric β-form of a prion protein which has more β-form than α-helix structure and retains solubility in aqueous solution in the absence of a denaturant.

2. A purified monomeric β-form of a prion protein which has more β-form than α-helix structure and retains solubility in aqueous solution in the absence of a denaturant and which is non-aggregated, but capable of forming an aggregated fibrous and/or amyloid form.

3. A purified monomeric β-form of a prion protein which has more β-form than α-helix structure and retains solubility in aqueous solution in the absence of a denaturant and which is non-aggregated but is capable of forming an aggregated fibrous and/or amyloid form on exposure to denaturant.

4. A purified monomeric β-form of a prion protein which has more β-form than α-helix structure and retains solubility in aqueous solution in the absence of a denaturant wherein the β-form of the prior protein will interconvert between predominantly α-helical form of a prion protein and said β-form of a prion protein when in aqueous solution at a concentration of more than 1 mg/ml and in the absence of a denaturant.

5. A purified monomeric β-form of a prion protein which has more β-form than α-helix structure and retains solubility in aqueous solution in the absence of a denaturant wherein the β-form of the prion protein will interconvert between predominantly α-helical form of a prion protein and said β-form of the prion protein when in aqueous solution at a concentration of at least 12 mg/ml and in the absence of a denaturant.

* * * * *

SEQUENCE LISTING

<160> NUMBER OF SEQ ID NOS: 37

<210> SEQ ID NO 1
<211> LENGTH: 253
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
            20                  25                  30

```
Thr Gly Gly Ser Arg Tyr Pro Gly Gln Gly Ser Pro Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 2
<211> LENGTH: 253
<212> TYPE: PRT
<213> ORGANISM: Pan troglodytes

<400> SEQUENCE: 2

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160
```

Val Tyr Tyr Arg Pro Met Asp Gln Tyr Ser Ser Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 3
<211> LENGTH: 253
<212> TYPE: PRT
<213> ORGANISM: Pongo pygmaeus

<400> SEQUENCE: 3

Met Ala Asn Leu Gly Cys Trp Met Leu Val Leu Phe Val Ala Thr Trp
1               5                   10                  15

Ser Asn Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Asn Asp
    130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 4
<211> LENGTH: 253
<212> TYPE: PRT

-continued

<213> ORGANISM: Gorilla gorilla

<400> SEQUENCE: 4

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 5
<211> LENGTH: 245
<212> TYPE: PRT
<213> ORGANISM: Cercopithecus aethiops

<400> SEQUENCE: 5

Met Ala Asn Leu Gly Cys Trp Met Leu Val Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Gly Gly Gly Thr His Asn Gln Trp His Lys Pro Ser Lys
                85                  90                  95

Pro Lys Thr Ser Met Lys His Met Ala Gly Ala Ala Ala Ala Gly Ala

```
                100               105              110
Val Val Gly Gly Leu Gly Gly Tyr Met Leu Gly Ser Ala Met Ser Arg
            115               120              125

Pro Leu Ile His Phe Gly Asn Asp Tyr Glu Asp Arg Tyr Tyr Arg Glu
    130               135              140

Asn Met Tyr Arg Tyr Pro Asn Gln Val Tyr Tyr Arg Pro Val Asp Gln
145               150              155              160

Tyr Ser Asn Gln Asn Asn Phe Val His Asp Cys Val Asn Ile Thr Ile
                165              170              175

Lys Gln His Thr Val Thr Thr Thr Lys Gly Glu Asn Phe Thr Glu
                180              185              190

Thr Asp Val Lys Met Met Glu Arg Val Val Glu Gln Met Cys Ile Thr
                195              200              205

Gln Tyr Glu Lys Glu Ser Gln Ala Tyr Tyr Gln Arg Gly Ser Ser Met
    210               215              220

Val Leu Phe Ser Ser Pro Pro Val Ile Leu Leu Ile Ser Phe Leu Ile
225               230              235              240

Phe Leu Ile Val Gly
            245

<210> SEQ ID NO 6
<211> LENGTH: 260
<212> TYPE: PRT
<213> ORGANISM: Saimiri sciureus

<400> SEQUENCE: 6

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly Trp
    50                  55                  60

Gly Gln Pro His Gly Gly Gly Trp Gly Gln Pro His Gly Gly Gly Trp
65                  70                  75                  80

Gly Gln Pro His Gly Gly Gly Trp Gly Gln Pro His Gly Gly Gly Trp
                85                  90                  95

Gly Gln Gly Gly Gly Thr His Asn Gln Trp Asn Lys Pro Ser Lys Pro
            100                 105                 110

Lys Thr Asn Met Lys His Met Ala Gly Ala Ala Ala Gly Ala Val
    115                 120                 125

Val Gly Gly Leu Gly Gly Tyr Met Leu Gly Ser Ala Met Ser Arg Pro
130                 135                 140

Leu Ile His Phe Gly Asn Asp Tyr Glu Asp Arg Tyr Tyr Arg Glu Asn
145                 150                 155                 160

Met Tyr Arg Tyr Pro Ser Gln Val Tyr Tyr Arg Pro Val Asp Gln Tyr
                165                 170                 175

Ser Asn Gln Asn Asn Phe Val His Asp Cys Val Asn Val Thr Ile Lys
            180                 185                 190

Gln His Thr Val Thr Thr Thr Lys Gly Glu Asn Phe Thr Glu Thr
    195                 200                 205

Asp Val Lys Met Met Glu Arg Val Val Glu Gln Met Cys Ile Thr Gln
210                 215                 220
```

```
Tyr Glu Lys Glu Ser Gln Ala Tyr Tyr Gln Arg Gly Ser Ser Met Val
225                 230                 235                 240

Leu Phe Ser Ser Pro Pro Val Ile Leu Leu Ile Ser Phe Leu Ile Phe
                245                 250                 255

Leu Ile Val Gly
            260

<210> SEQ ID NO 7
<211> LENGTH: 253
<212> TYPE: PRT
<213> ORGANISM: Macaca mulatta

<400> SEQUENCE: 7

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp His Lys Pro Ser Lys Pro Lys Thr Ser Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 8
<211> LENGTH: 253
<212> TYPE: PRT
<213> ORGANISM: Hylobates sp.

<400> SEQUENCE: 8

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30
```

Thr Gly Gly Ser Arg Tyr Pro Gly Gln Gly Ser Pro Gly Asn Arg
    35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                    85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Ser Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
    195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 9
<211> LENGTH: 253
<212> TYPE: PRT
<213> ORGANISM: Macaca sp.

<400> SEQUENCE: 9

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Asn Arg
    35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                    85                  90                  95

Asn Gln Trp His Lys Pro Ser Lys Pro Lys Thr Ser Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Leu Ile His Phe Gly Asn Asp
    130                 135                 140

Tyr Glu Asp Arg Tyr Tyr Arg Glu Asn Met Tyr Arg Tyr Pro Asn Gln
145                 150                 155                 160

```
Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 10
<211> LENGTH: 253
<212> TYPE: PRT
<213> ORGANISM: Macaca sp.

<400> SEQUENCE: 10

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Asn Gln Trp His Lys Pro Ser Lys Pro Lys Thr Ser Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Leu Ile His Phe Gly Asn Asp
        130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 11
<211> LENGTH: 253
<212> TYPE: PRT
```

<210> ORGANISM: Macaca sp.

<400> SEQUENCE: 11

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp His Lys Pro Ser Lys Pro Lys Thr Ser Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 12
<211> LENGTH: 253
<212> TYPE: PRT
<213> ORGANISM: Macaca sp.

<400> SEQUENCE: 12

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp His Lys Pro Ser Lys Pro Lys Thr Ser Met Lys His Met

-continued

```
                100                 105                 110
Ala Gly Ala Ala Ala Gly Ala Val Val Gly Gly Leu Gly Gly Tyr
            115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
            195                 200                 205

Val Val Glu Gln Met Cys Ile Thr Gln Tyr Glu Lys Glu Ser Gln Ala
            210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 13
<211> LENGTH: 252
<212> TYPE: PRT
<213> ORGANISM: Callithrix sp.

<400> SEQUENCE: 13

Met Ala Asn Leu Gly Cys Trp Met Leu Phe Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Trp Gly Gln Pro His Gly Gly Gly Trp
    50                  55                  60

Gly Gln Pro His Gly Gly Gly Trp Gly Gln Pro His Gly Gly Gly Trp
65                  70                  75                  80

Gly Gln Pro His Gly Gly Gly Trp Gly Gln Gly Gly Thr His Ser
                85                  90                  95

Gln Trp Asn Lys Pro Ser Lys Pro Lys Thr Asn Met Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Leu Ile His Phe Gly Asn Asp Tyr
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Asn Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Ile Thr Gln Tyr Glu Lys Glu Ser Gln Ala Tyr
    210                 215                 220
```

Tyr Gln Arg Gly Ser Ser Met Val Leu Phe Ser Ser Pro Val Ile
225                 230                 235                 240

Leu Leu Ile Ser Phe Leu Ile Phe Leu Ile Val Gly
            245                 250

<210> SEQ ID NO 14
<211> LENGTH: 253
<212> TYPE: PRT
<213> ORGANISM: Papio hamadryas

<400> SEQUENCE: 14

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp His Lys Pro Ser Lys Pro Lys Thr Ser Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 15
<211> LENGTH: 245
<212> TYPE: PRT
<213> ORGANISM: Cercopithecus diana

<400> SEQUENCE: 15

Met Ala Asn Leu Gly Cys Trp Met Leu Val Val Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

```
Tyr Pro Pro Gln Gly Gly Gly Trp Gly Gln Pro His Gly Gly
    50              55                  60

Trp Gly Gln Pro His Gly Gly Trp Gly Gln Pro His Gly Gly
65              70                  75                  80

Trp Gly Gln Gly Gly Gly Thr His Asn Gln Trp His Lys Pro Ser Lys
                85                  90                  95

Pro Lys Thr Ser Met Lys His Met Ala Gly Ala Ala Ala Gly Ala
            100                 105                 110

Val Val Gly Gly Leu Gly Gly Tyr Met Leu Gly Ser Ala Met Ser Arg
        115                 120                 125

Pro Leu Ile His Phe Gly Asn Asp Tyr Glu Asp Arg Tyr Tyr Arg Glu
        130                 135                 140

Asn Met Tyr Arg Tyr Pro Asn Gln Val Tyr Arg Pro Val Asp Gln
145                 150                 155                 160

Tyr Ser Asn Gln Asn Asn Phe Val His Asp Cys Val Asn Ile Thr Ile
                165                 170                 175

Lys Gln His Thr Val Thr Thr Thr Lys Gly Glu Asn Phe Thr Glu
            180                 185                 190

Thr Asp Val Lys Met Met Glu Arg Val Val Glu Gln Met Cys Ile Thr
        195                 200                 205

Gln Tyr Glu Lys Glu Ser Gln Ala Tyr Tyr Gln Arg Gly Ser Ser Met
    210                 215                 220

Val Leu Phe Ser Ser Pro Pro Val Ile Leu Leu Ile Ser Phe Leu Ile
225                 230                 235                 240

Phe Leu Ile Val Gly
                245

<210> SEQ ID NO 16
<211> LENGTH: 253
<212> TYPE: PRT
<213> ORGANISM: Colobus guereza

<400> SEQUENCE: 16

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50              55                  60

Trp Gly Gln Pro His Gly Gly Trp Gly Gln Pro His Gly Gly Gly
65              70                  75                  80

Trp Gly Gln Pro His Gly Gly Gly Trp Gly Gln Gly Gly Thr His
                85                  90                  95

Ser Gln Trp Asn Lys Pro Ser Lys Pro Lys Thr Ser Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175
```

-continued

```
His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 17
<211> LENGTH: 252
<212> TYPE: PRT
<213> ORGANISM: Cebus sp.

<400> SEQUENCE: 17

```
Met Ala Asn Leu Gly Cys Trp Met Leu Val Leu Phe Val Ala Thr Trp
  1               5                  10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Leu
        35                  40                  45

Tyr Pro Pro Gln Gly Gly Trp Gly Gln Pro His Gly Gly Ser Trp
    50                  55                  60

Gly Gln Pro His Gly Gly Gly Trp Gly Gln Pro His Gly Gly Gly Trp
 65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Ser Met Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Leu Ile His Phe Gly Asn Asp Tyr
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr
            180                 185                 190

Lys Gly Glu Asn Phe Thr Glu Thr Asp Val Lys Met Met Glu Arg Val
        195                 200                 205

Val Glu Gln Met Cys Ile Thr Gln Tyr Glu Arg Glu Ser Gln Ala Tyr
    210                 215                 220

Tyr Gln Arg Gly Ser Ser Met Val Leu Phe Ser Ser Pro Pro Val Ile
225                 230                 235                 240

Leu Leu Ile Ser Phe Leu Ile Phe Leu Ile Val Gly
                245                 250
```

<210> SEQ ID NO 18
<211> LENGTH: 253
<212> TYPE: PRT
<213> ORGANISM: Presbytis francoisi

<400> SEQUENCE: 18

-continued

```
Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Gly Trp Gly Gln Pro His Gly Gly Gly
     50                  55                  60

Trp Gly Gln Pro His Gly Gly Trp Gly Gln Pro His Gly Gly Gly
 65                  70                  75                  80

Trp Gly Gln Pro His Gly Gly Trp Gly Gln Gly Gly Thr His
                 85                  90                  95

Ser Gln Trp Asn Lys Pro Ser Lys Pro Lys Thr Ser Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Leu Ile His Phe Gly Asn Asp
130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Lys Glu Ser Gln Ala
210                 215                 220

Tyr Tyr Gln Arg Gly Ser Ser Met Val Phe Phe Ser Ser Pro Pro Val
225                 230                 235                 240

Ile Leu Leu Ile Ser Phe Leu Ile Phe Leu Ile Val Gly
                245                 250

<210> SEQ ID NO 19
<211> LENGTH: 253
<212> TYPE: PRT
<213> ORGANISM: Hylobates syndactylus

<400> SEQUENCE: 19

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Gly Trp Gly Gln Pro His Gly Gly Gly
     50                  55                  60

Trp Gly Gln Pro His Gly Gly Trp Gly Gln Pro His Gly Gly Gly
 65                  70                  75                  80

Trp Gly Gln Pro His Gly Gly Trp Gly Gln Gly Gly Thr His
                 85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
```

-continued

```
                115                 120                 125
Met Leu Gly Ser Ala Met Ser Arg Pro Ile Ile His Phe Gly Ser Asp
        130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Gln Tyr Ser Ser Gln Asn Asn Phe Val
                165                 170                 175
His Asp Cys Val Asn Ile Thr Ile Lys Gln His Thr Val Thr Thr Thr
            180                 185                 190
Thr Lys Gly Glu Asn Phe Thr Glu Thr Asp Val Lys Met Met Glu Arg
        195                 200                 205
Val Val Glu Gln Met Cys Ile Thr Gln Tyr Glu Arg Glu Ser Gln Ala
    210                 215                 220
Tyr Tyr Gln Arg Gly Ser Ser Met Val Leu Phe Ser Ser Pro Pro Val
225                 230                 235                 240
Ile Leu Leu Ile Ser Phe Leu Ile Phe Leu Ile Val Gly
                245                 250

<210> SEQ ID NO 20
<211> LENGTH: 254
<212> TYPE: PRT
<213> ORGANISM: Mus sp.

<400> SEQUENCE: 20

Met Ala Asn Leu Gly Tyr Trp Leu Leu Ala Leu Phe Val Thr Met Trp
  1               5                  10                  15
Thr Asp Val Gly Leu Cys Lys Lys Arg Pro Lys Pro Gly Gly Trp Asn
                 20                  25                  30
Thr Gly Gly Ser Arg Tyr Pro Gly Gln Gly Ser Pro Gly Gly Asn Arg
             35                  40                  45
Tyr Pro Pro Gln Gly Thr Gly Trp Gly Gln Pro His Gly Gly Ser Trp
         50                  55                  60
Gly Gln Pro His Gly Gly Ser Trp Gly Gln Pro His Gly Gly Gly Trp
 65                  70                  75                  80
Gly Gln Pro His Gly Gly Gly Trp Gly Gln Gly Gly Gly Thr His Asn
                 85                  90                  95
Gln Trp Asn Lys Pro Ser Lys Pro Lys Thr Asn Leu Lys His Val Ala
                100                 105                 110
Gly Ala Ala Ala Ala Gly Ala Val Val Gly Gly Leu Gly Gly Tyr Met
            115                 120                 125
Leu Gly Ser Ala Val Ser Arg Pro Met Ile His Phe Gly Asn Asp Trp
        130                 135                 140
Glu Asp Arg Tyr Tyr Arg Glu Asn Met Tyr Arg Tyr Pro Asn Gln Val
145                 150                 155                 160
Tyr Tyr Arg Pro Val Asp Gln Tyr Ser Asn Gln Asn Asn Phe Val His
                165                 170                 175
Asp Cys Val Asn Ile Thr Ile Lys Gln His Thr Val Thr Thr Thr Thr
            180                 185                 190
Lys Gly Glu Asn Phe Thr Glu Thr Asp Val Lys Met Met Glu Arg Val
        195                 200                 205
Val Glu Gln Met Cys Val Thr Gln Tyr Gln Lys Glu Ser Gln Ala Tyr
    210                 215                 220
Tyr Asp Gly Arg Arg Ser Ser Thr Val Leu Phe Ser Ser Pro Pro
225                 230                 235                 240
```

-continued

```
Val Ile Leu Leu Ile Ser Phe Leu Ile Phe Leu Ile Val Gly
                245                 250

<210> SEQ ID NO 21
<211> LENGTH: 254
<212> TYPE: PRT
<213> ORGANISM: Mus sp.

<400> SEQUENCE: 21

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Thr Gly Trp Gly Gln Pro His Gly Gly Ser Trp
    50                  55                  60

Gly Gln Pro His Gly Gly Ser Trp Gly Gln Pro His Gly Gly Gly Trp
65                  70                  75                  80

Gly Gln Pro His Gly Gly Trp Gly Gln Gly Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 22
<211> LENGTH: 254
<212> TYPE: PRT
<213> ORGANISM: Mus sp.

<400> SEQUENCE: 22

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Thr Gly Trp Gly Gln Pro His Gly Gly Ser Trp
    50                  55                  60
```

-continued

```
Gly Gln Pro His Gly Gly Ser Trp Gly Gln Pro His Gly Gly Trp
 65                  70                  75                  80

Gly Gln Pro His Gly Gly Trp Gly Gln Gly Gly Gly Thr His Asn
                 85                  90                  95

Gln Trp Asn Lys Pro Ser Lys Pro Lys Thr Asn Phe Lys His Val Ala
            100                 105                 110

Gly Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Val Thr Thr Thr
                180                 185                 190

Lys Gly Glu Asn Phe Thr Glu Thr Asp Val Lys Met Met Glu Arg Val
                195                 200                 205

Val Glu Gln Met Cys Val Thr Gln Tyr Gln Lys Glu Ser Gln Ala Tyr
        210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250
```

<210> SEQ ID NO 23
<211> LENGTH: 254
<212> TYPE: PRT
<213> ORGANISM: Mesocricetus auratus

<400> SEQUENCE: 23

```
Met Ala Asn Leu Ser Tyr Trp Leu Leu Ala Leu Phe Val Ala Thr Trp
  1               5                  10                  15

Thr Asp Val Gly Leu Cys Lys Lys Arg Pro Lys Pro Gly Gly Trp Asn
                 20                  25                  30

Thr Gly Gly Ser Arg Tyr Pro Gly Gln Gly Ser Pro Gly Gly Asn Arg
            35                  40                  45

Tyr Pro Pro Gln Gly Gly Thr Gly Trp Gly Gln Pro His Gly Gly Gly
 50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Asn Gln Trp Asn Lys Pro Ser Lys Pro Lys Thr Asn Met Lys His Val
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Leu His Phe Gly Asn Asp
130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Thr
                180                 185                 190
```

```
Thr Lys Gly Glu Asn Phe Thr Thr Asp Val Lys Met Met Glu Arg
        195                 200                 205

Val Val Glu Gln Met Cys Val Thr Gln Tyr Gln Lys Glu Ser Gln Ala
        210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 24
<211> LENGTH: 264
<212> TYPE: PRT
<213> ORGANISM: Bos taurus

<400> SEQUENCE: 24

Met Val Lys Ser His Ile Gly Ser Trp Met Leu Val Leu Phe Val Ala
  1               5                  10                  15

Met Trp Ser Asp Val Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
     50                  55                  60

Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Pro
                 85                  90                  95

His Gly Gly Gly Trp Gly Gln Gly Gly Thr Gly Asn Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Gly Leu Gly Gly Tyr Met Leu Gly Ser Ala
        130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Glu Thr Asp Ile Lys Met Met Glu Arg Val Val Glu Gln Met
210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Val Ile Leu Leu Ile Ser
                245                 250                 255

Phe Leu Ile Phe Leu Ile Val Gly
            260

<210> SEQ ID NO 25
<211> LENGTH: 256
<212> TYPE: PRT
<213> ORGANISM: Ovis sp.

<400> SEQUENCE: 25
```

```
Met Val Lys Ser His Ile Gly Ser Trp Met Leu Val Leu Phe Val Ala
 1               5                  10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
        50                  55                  60

Gly Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
            115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 26
<211> LENGTH: 256
<212> TYPE: PRT
<213> ORGANISM: Antilocapra americana

<400> SEQUENCE: 26

Met Val Lys Ser His Ile Gly Ser Trp Met Leu Val Leu Phe Val Ala
 1               5                  10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
        50                  55                  60

Gly Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
```

```
              115                 120                 125
Gly Gly Tyr Met Leu Gly Ser Ala Met Asn Arg Pro Leu Ile His Phe
        130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
        210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 27
<211> LENGTH: 264
<212> TYPE: PRT
<213> ORGANISM: Tragelaphus strepsiceros

<400> SEQUENCE: 27

Met Val Lys Ser His Ile Gly Ser Trp Met Leu Val Leu Phe Val Ala
  1               5                  10                  15

Met Trp Ser Asp Val Ala Leu Cys Lys Lys Arg Pro Lys Pro Gly Gly
                 20                  25                  30

Gly Trp Asn Thr Gly Gly Ser Arg Tyr Pro Gly Gln Gly Ser Pro Gly
             35                  40                  45

Gly Asn Arg Tyr Pro Ser Gln Gly Gly Gly Trp Gly Gln Pro His
         50                  55                  60

Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Pro
                 85                  90                  95

His Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Gly Leu Gly Gly Tyr Met Leu Gly Ser Ala
        130                 135                 140

Met Ser Arg Pro Leu Ile His Phe Gly Ser Asp Tyr Glu Asp Arg Tyr
145                 150                 155                 160

Tyr Arg Glu Asn Met Tyr Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Gln His Thr Val Thr Thr Thr Thr Lys Gly Glu Asn
            195                 200                 205

Phe Thr Glu Thr Asp Ile Lys Met Met Glu Arg Val Val Glu Gln Met
        210                 215                 220

Cys Ile Thr Gln Tyr Gln Arg Glu Ser Glu Ala Tyr Tyr Gln Arg Gly
225                 230                 235                 240
```

```
Ala Ser Val Ile Leu Phe Ser Ser Pro Val Ile Leu Leu Ile Ser
                245                 250                 255

Phe Leu Ile Phe Leu Ile Val Gly
            260
```

<210> SEQ ID NO 28
<211> LENGTH: 256
<212> TYPE: PRT
<213> ORGANISM: Capra hircus

<400> SEQUENCE: 28

```
Met Val Lys Ser His Ile Gly Ser Trp Met Leu Val Leu Phe Val Ala
 1               5                  10                  15

Met Trp Ser Asp Val Gly Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
        50                  55                  60

Gly Gly Gly Gly Trp Gly Gln Pro His Gly Gly Trp Gly Gln Pro
 65                 70                  75                  80

His Gly Gly Gly Trp Gly Gln Pro His Gly Gly Trp Gly Gln Gly
                85                  90                  95

Gly Ser His Ser Gln Trp Asn Lys Pro Ser Lys Pro Lys Thr Asn Met
                100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
            130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
                180                 185                 190

Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
210                 215                 220

Ser Gln Ala Tyr Tyr Gln Arg Gly Ala Ser Val Ile Leu Phe Ser Pro
225                 230                 235                 240

Pro Pro Val Ile Leu Leu Ile Ser Phe Leu Ile Phe Leu Ile Val Gly
                245                 250                 255
```

<210> SEQ ID NO 29
<211> LENGTH: 257
<212> TYPE: PRT
<213> ORGANISM: Sus sp.

<400> SEQUENCE: 29

```
Met Val Lys Ser His Ile Gly Gly Trp Met Leu Val Leu Phe Val Ala
 1               5                  10                  15

Ala Trp Ser Asp Ile Gly Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
            35                  40                  45
```

-continued

```
Gly Asn Arg Tyr Pro Pro Gln Gly Gly Gly Trp Gly Gln Pro His
 50                  55                  60

Gly Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Gly
                 85                  90                  95

Gly Gly Ser His Gly Gln Trp Asn Lys Pro Ser Lys Pro Lys Thr Asn
            100                 105                 110

Met Lys His Val Ala Gly Ala Ala Ala Ala Gly Ala Val Val Gly Gly
            115                 120                 125

Leu Gly Gly Tyr Met Leu Gly Ser Ala Met Ser Arg Pro Leu Ile His
        130                 135                 140

Phe Gly Ser Asp Tyr Glu Asp Arg Tyr Tyr Arg Glu Asn Met Tyr Arg
145                 150                 155                 160

Tyr Pro Asn Gln Val Tyr Tyr Arg Pro Val Asp Gln Tyr Ser Asn Gln
                165                 170                 175

Asn Ser Phe Val His Asp Cys Val Asn Ile Thr Val Lys Gln His Thr
            180                 185                 190

Val Thr Thr Thr Lys Gly Glu Asn Phe Thr Glu Thr Asp Val Lys
        195                 200                 205

Met Ile Glu Arg Val Val Glu Gln Met Cys Ile Thr Gln Tyr Gln Lys
    210                 215                 220

Glu Tyr Glu Ala Tyr Ala Gln Arg Gly Ala Ser Val Ile Leu Phe Ser
225                 230                 235                 240

Ser Pro Pro Val Ile Leu Leu Ile Ser Phe Leu Ile Phe Leu Ile Val
                245                 250                 255

Gly

<210> SEQ ID NO 30
<211> LENGTH: 257
<212> TYPE: PRT
<213> ORGANISM: Mustela sp.

<400> SEQUENCE: 30

Met Val Lys Ser His Ile Gly Ser Trp Leu Leu Val Leu Phe Val Ala
 1               5                  10                  15

Thr Trp Ser Asp Ile Gly Phe Cys Lys Lys Arg Pro Lys Pro Gly Gly
                 20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
 50                  55                  60

Gly Gly Gly Gly Trp Gly Gln Pro His Gly Gly Gly Trp Gly Gln Pro
 65                  70                  75                  80

His Gly Gly Gly Trp Gly Gln Pro His Gly Gly Gly Trp Gly Gln Gly
                 85                  90                  95

Gly Gly Ser His Gly Gln Trp Gly Lys Pro Ser Lys Pro Lys Thr Asn
            100                 105                 110

Met Lys His Val Ala Gly Ala Ala Ala Ala Gly Ala Val Val Gly Gly
            115                 120                 125

Leu Gly Gly Tyr Met Leu Gly Ser Ala Met Ser Arg Pro Leu Ile His
        130                 135                 140

Phe Gly Asn Asp Tyr Glu Asp Arg Tyr Tyr Arg Glu Asn Met Tyr Arg
145                 150                 155                 160
```

```
Tyr Pro Asn Gln Val Tyr Tyr Lys Pro Val Asp Gln Tyr Ser Asn Gln
                165                 170                 175

Asn Asn Leu Val His Asp Cys Val Asn Ile Thr Val Lys Gln His Thr
            180                 185                 190

Val Thr Thr Thr Thr Lys Gly Glu Asn Phe Thr Glu Thr Asp Met Lys
        195                 200                 205

Ile Met Glu Arg Val Val Glu Gln Met Cys Val Thr Gln Tyr Gln Gln
    210                 215                 220

Glu Ser Glu Ala Tyr Tyr Gln Arg Gly Ala Ser Ala Ile Leu Phe Ser
225                 230                 235                 240

Pro Pro Pro Val Ile Leu Leu Ile Ser Leu Leu Ile Leu Leu Ile Val
                245                 250                 255

Gly

<210> SEQ ID NO 31
<211> LENGTH: 256
<212> TYPE: PRT
<213> ORGANISM: Canis familiaris

<400> SEQUENCE: 31

Met Val Lys Ser His Ile Gly Gly Trp Ile Leu Leu Phe Val Ala Thr
  1               5                  10                  15

Trp Ser Asp Val Gly Leu Cys Lys Lys Arg Pro Lys Pro Gly Gly Trp
                 20                  25                  30

Asn Thr Gly Gly Gly Ser Arg Tyr Pro Gly Gln Gly Ser Pro Gly Gly
             35                  40                  45

Asn Arg Tyr Pro Pro Gln Gly Gly Gly Trp Gly Gln Pro His Gly
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Gly Gly
                 85                  90                  95

Gly Ser His Ser Gln Trp Gly Lys Pro Asn Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Glu Gln Val Tyr Tyr Pro Pro Val Asp Gln Tyr Ser Asn Gln Asn
                165                 170                 175

Asn Phe Val Arg Asp Cys Val Asn Ile Thr Val Lys Gln His Thr Val
            180                 185                 190

Thr Thr Thr Thr Lys Gly Glu Asn Phe Thr Glu Thr Asp Met Lys Ile
        195                 200                 205

Met Glu Arg Val Val Glu Gln Met Cys Val Thr Gln Tyr Gln Lys Glu
    210                 215                 220

Ser Glu Ala Tyr Tyr Gln Arg Gly Ala Ser Ala Ile Leu Phe Ser Pro
225                 230                 235                 240

Pro Pro Val Ile Leu Leu Ile Ser Leu Leu Ile Leu Leu Ile Val Gly
                245                 250                 255

<210> SEQ ID NO 32
<211> LENGTH: 252
```

```
<212> TYPE: PRT
<213> ORGANISM: Oryctolagus cuniculus

<400> SEQUENCE: 32

Met Ala His Leu Gly Tyr Trp Met Leu Leu Phe Val Ala Thr Trp
 1               5                  10                  15

Ser Asp Val Gly Leu Cys Lys Lys Arg Pro Lys Pro Gly Gly Trp
                20                  25                  30

Asn Thr Gly Gly Ser Arg Tyr Pro Gly Gln Ser Ser Pro Gly Gly Asn
            35                  40                  45

Arg Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Thr His Asn
                85                  90                  95

Gln Trp Gly Lys Pro Ser Lys Pro Lys Thr Ser Met Lys His Val Ala
               100                 105                 110

Gly Ala Ala Ala Gly Ala Val Val Gly Gly Leu Gly Gly Tyr Met
            115                 120                 125

Leu Gly Ser Ala Met Ser Arg Pro Leu Ile His Phe Gly Asn Asp Tyr
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Ser Phe Val His
                165                 170                 175

Asp Cys Val Asn Ile Thr Val Lys Gln His Thr Val Thr Thr Thr Thr
            180                 185                 190

Lys Gly Glu Asn Phe Thr Glu Thr Asp Ile Lys Ile Met Glu Arg Val
    195                 200                 205

Val Glu Gln Met Cys Ile Thr Gln Tyr Gln Gln Glu Ser Gln Ala Ala
210                 215                 220

Tyr Gln Arg Ala Ala Gly Val Val Leu Phe Ser Ser Pro Pro Val Ile
225                 230                 235                 240

Leu Leu Ile Ser Phe Leu Ile Phe Leu Ile Val Gly
                245                 250

<210> SEQ ID NO 33
<211> LENGTH: 259
<212> TYPE: PRT
<213> ORGANISM: Trichosurus vulpecula

<400> SEQUENCE: 33

Met Gly Lys Ile Gln Leu Gly Tyr Trp Ile Leu Val Leu Phe Ile Val
 1               5                  10                  15

Thr Trp Ser Asp Leu Gly Leu Cys Lys Lys Pro Lys Pro Arg Pro Gly
                20                  25                  30

Gly Gly Trp Asn Ser Gly Gly Ser Asn Arg Tyr Pro Gly Gln Pro Gly
            35                  40                  45

Ser Pro Gly Gly Asn Arg Tyr Pro Gly Trp Gly His Pro Gln Gly Gly
    50                  55                  60

Gly Thr Asn Trp Gly Gln Pro His Pro Gly Gly Ser Asn Trp Gly Gln
 65                  70                  75                  80

Pro His Pro Gly Gly Ser Ser Trp Gly Gln Pro His Gly Gly Ser Asn
                85                  90                  95
```

```
Trp Gly Gln Gly Gly Tyr Asn Lys Trp Lys Pro Asp Lys Pro Lys Thr
                100                 105                 110

Asn Leu Lys His Val Ala Gly Ala Ala Ala Gly Ala Val Val Gly
        115                 120                 125

Gly Leu Gly Gly Tyr Met Leu Gly Ser Ala Met Ser Arg Pro Val Ile
        130                 135                 140

His Phe Gly Asn Glu Tyr Glu Asp Arg Tyr Tyr Arg Glu Asn Gln Tyr
145                 150                 155                 160

Arg Tyr Pro Asn Gln Val Met Tyr Arg Pro Ile Asp Gln Tyr Ser Ser
                165                 170                 175

Gln Asn Asn Phe Val His Asp Cys Val Asn Ile Thr Val Lys Gln His
                180                 185                 190

Thr Thr Thr Thr Thr Thr Lys Gly Glu Asn Phe Thr Glu Thr Asp Ile
                195                 200                 205

Lys Ile Met Glu Arg Val Val Glu Gln Met Cys Ile Thr Gln Tyr Gln
210                 215                 220

Ala Glu Tyr Glu Ala Ala Gln Arg Ala Tyr Asn Met Ala Phe Phe
225                 230                 235                 240

Ser Ala Pro Pro Val Thr Leu Leu Phe Leu Ser Phe Leu Ile Phe Leu
                245                 250                 255

Ile Val Ser
```

<210> SEQ ID NO 34
<211> LENGTH: 277
<212> TYPE: PRT
<213> ORGANISM: Gallus gallus

<400> SEQUENCE: 34

```
Met Pro Ala Ala Met Ala Arg Leu Leu Thr Thr Cys Cys Leu Leu Ala
 1               5                  10                  15

Leu Leu Leu Ala Ala Cys Thr Asp Val Ala Leu Ser Lys Lys Gly Lys
              20                  25                  30

Gly Lys Pro Ser Gly Gly Gly Trp Gly Ala Gly Ser His Arg Gln Pro
          35                  40                  45

Ser Tyr Pro Arg Gln Pro Gly Tyr Pro His Asn Pro Gly Tyr Pro His
     50                  55                  60

Asn Pro Gly Tyr Pro His Asn Pro Gly Tyr Pro His Asn Pro Gly Tyr
 65                  70                  75                  80

Pro His Asn Pro Gly Tyr Pro Gln Asn Pro Gly Tyr Pro His Asn Pro
                  85                  90                  95

Gly Tyr Pro Gly Trp Gly Gln Gly Tyr Asn Pro Ser Ser Gly Gly Ser
                100                 105                 110

Tyr His Asn Gln Lys Pro Trp Lys Pro Pro Lys Thr Asn Phe Lys His
            115                 120                 125

Val Ala Gly Ala Ala Ala Gly Ala Val Val Gly Gly Leu Gly Gly
        130                 135                 140

Tyr Ala Met Gly Arg Val Met Ser Gly Met Asn Tyr His Phe Asp Ser
145                 150                 155                 160

Pro Asp Glu Tyr Arg Trp Trp Ser Glu Asn Ser Ala Arg Tyr Pro Asn
                165                 170                 175

Arg Val Tyr Tyr Arg Asp Tyr Ser Ser Pro Val Pro Gln Asp Val Phe
                180                 185                 190

Val Ala Asp Cys Phe Asn Ile Thr Val Thr Glu Tyr Ser Ile Gly Pro
                195                 200                 205
```

```
Ala Ala Lys Lys Asn Thr Ser Glu Ala Val Ala Ala Asn Gln Thr
        210                 215                 220

Glu Val Glu Met Glu Asn Lys Val Val Thr Lys Val Ile Arg Glu Met
225                 230                 235                 240

Cys Val Gln Gln Tyr Arg Glu Tyr Arg Leu Ala Ser Gly Ile Gln Leu
                245                 250                 255

His Pro Ala Asp Thr Trp Leu Ala Val Leu Leu Leu Leu Thr Thr
            260                 265                 270

Leu Phe Ala Met His
        275

<210> SEQ ID NO 35
<211> LENGTH: 762
<212> TYPE: DNA
<213> ORGANISM: Homo sapiens

<400> SEQUENCE: 35
atggcgaacc ttggctgctg gatgctggtt ctctttgtgg ccacatggag tgacctgggc      60
ctctgcaaga agcgcccgaa gcctggagga tggaacactg ggggcagccg atacccgggg    120
cagggcagcc ctggaggcaa ccgctaccca cctcagggcg gtggtggctg ggggcagcct    180
catggtggtg gctgggggca gcctcatggt ggtggctggg ggcagcccca tggtggtggc    240 tgggacagc tcatggtgg tggctggggt caaggaggtg gcacccacag tcagtggaac      300
aagccgagta agccaaaaac caacatgaag cacatggctg gtgctgcagc agctggggca    360
gtggtggggg gccttggcgg ctacatgctg ggaagtgcca tgagcaggcc catcatacat    420
ttcggcagtg actatgagga ccgttactat cgtgaaaaca tgcaccgtta ccccaaccaa    480
gtgtactaca ggcccatgga tgagtacagc aaccagaaca actttgtgca cgactgcgtc    540
aatatcacaa tcaagcagca cacggtcacc acaaccacca aggggagaa cttcaccgag    600 accgacgtta agatgatgga gcgcgtggtt gagcagatgt gtatcaccca gtacgagagg    660
gaatctcagg cctattacca gagaggatcg agcatggtcc tcttctcctc tccacctgtg    720
atcctcctga tctctttcct catcttcctg atagtgggat ga                       762

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: N-terminal
      sense oligo

<400> SEQUENCE: 36
tttggatccg atgcaaggag gtggcaccca c                                   31

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: C-terminal
      antisense oligo

<400> SEQUENCE: 37
caagaagctt tcagctcgat cctctctgg                                      29
```